(12) United States Patent
Roninson et al.

(10) Patent No.: US 10,993,945 B2
(45) Date of Patent: *May 4, 2021

(54) CDK8-CDK19 SELECTIVE INHIBITORS AND THEIR USE IN ANTI-METASTATIC AND CHEMOPREVENTATIVE METHODS FOR CANCER

(71) Applicant: SENEX BIOTECHNOLOGY, INC., Columbia, SC (US)

(72) Inventors: Igor B Roninson, Lexington, SC (US); Donald C Porter, Columbia, SC (US)

(73) Assignee: SENEX BIOTECHNOLOGY, INC., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/065,083

(22) Filed: Mar. 9, 2016

(65) Prior Publication Data

US 2017/0071942 A1    Mar. 16, 2017

Related U.S. Application Data

(63) Continuation of application No. 13/757,682, filed on Feb. 1, 2013, now Pat. No. 9,321,737.

(51) Int. Cl.

| | | |
|---|---|---|
| *A61K 31/517* | (2006.01) |
| *A61K 45/06* | (2006.01) |
| *A61K 31/535* | (2006.01) |
| *A61K 31/495* | (2006.01) |
| *A61K 31/5377* | (2006.01) |
| *C07D 239/94* | (2006.01) |
| *C07D 401/12* | (2006.01) |
| *C07D 403/12* | (2006.01) |
| *C07D 413/12* | (2006.01) |
| *C12Q 1/6886* | (2018.01) |
| *G01N 33/574* | (2006.01) |

(52) U.S. Cl.
CPC .......... *A61K 31/517* (2013.01); *A61K 31/495* (2013.01); *A61K 31/535* (2013.01); *A61K 31/5377* (2013.01); *A61K 45/06* (2013.01); *C07D 239/94* (2013.01); *C07D 401/12* (2013.01); *C07D 403/12* (2013.01); *C07D 413/12* (2013.01); *C12Q 1/6886* (2013.01); *G01N 33/57415* (2013.01); *G01N 33/57449* (2013.01); *C12Q 2600/106* (2013.01); *C12Q 2600/118* (2013.01); *C12Q 2600/158* (2013.01); *G01N 2333/4739* (2013.01); *G01N 2333/91205* (2013.01)

(58) Field of Classification Search
CPC .................................................... A61K 31/517
See application file for complete search history.

(56) References Cited

PUBLICATIONS

Prevention and Treatment of Cancer, Leaf, 2004.*

* cited by examiner

*Primary Examiner* — Yong S. Chong
(74) *Attorney, Agent, or Firm* — Quarles & Brady LLP

(57) ABSTRACT

The invention relates to the compounds and methods for inhibiting the Cyclin-Dependent Kinase Inhibitor (CDKI) pathway. More particularly, the invention relates to compounds and methods for inhibiting the CDKI pathway for studies of and intervention in senescence-related and other CDKI-related diseases. The invention provides new compounds having improved solubility and/or potency, and methods for their use. In various aspects, the invention relates to the treatment of cancer. The invention provides methods for chemoprevention and prevention of tumor recurrence or metastasis. The invention further provides diagnostic techniques for treatment for certain cancer types. The invention utilizes specific inhibitors of CDK8/19 and/or measurement of CDK8 levels in a patient.

4 Claims, 23 Drawing Sheets

SNX2-1-150
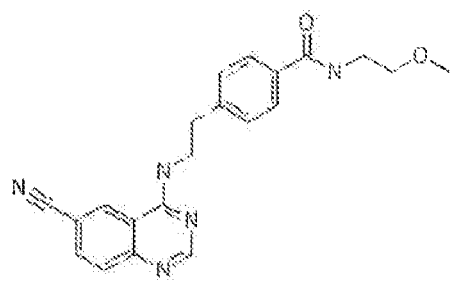
SNX2-1-151
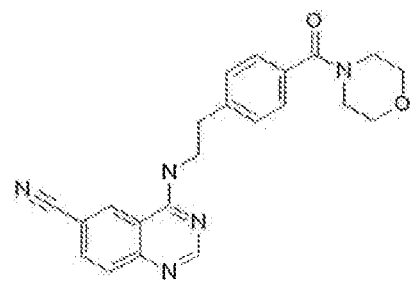
SNX2-1-152
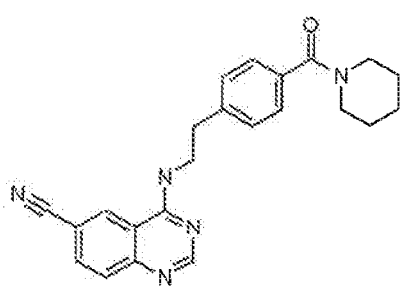
SNX2-1-153
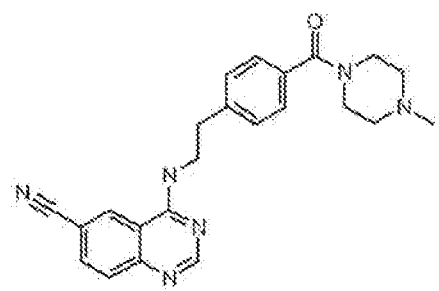
SNX2-1-154
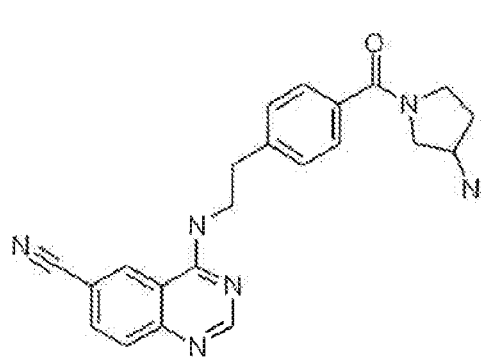
SNX2-1-155
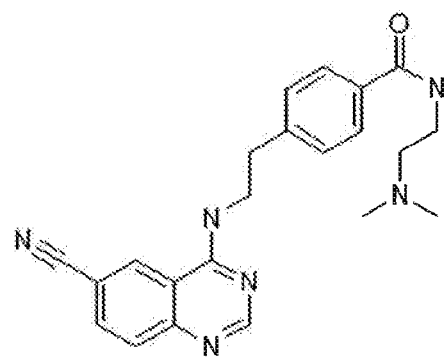
Fig. 1A SNX2-1-157
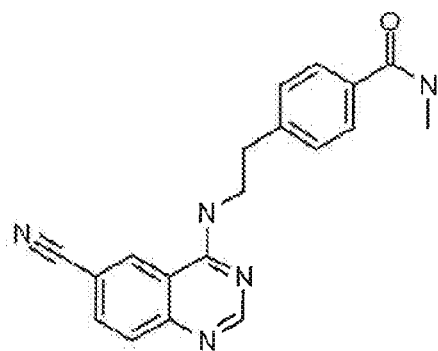
SNX2-1-158
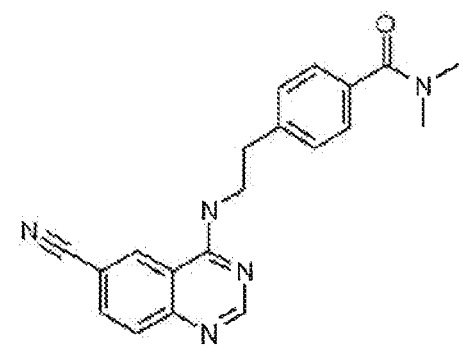
SNX2-1-162
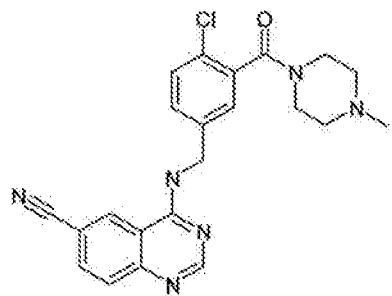
SNX2-1-163
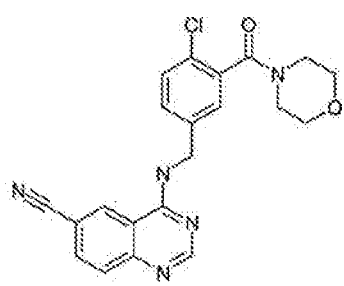
SNX2-1-164
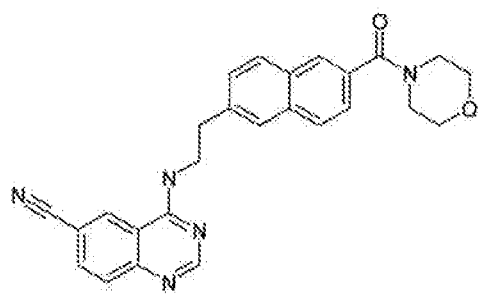
SNX2-1-165
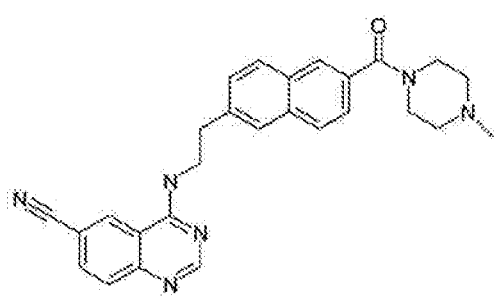
Fig. 1B SNX2-1-166
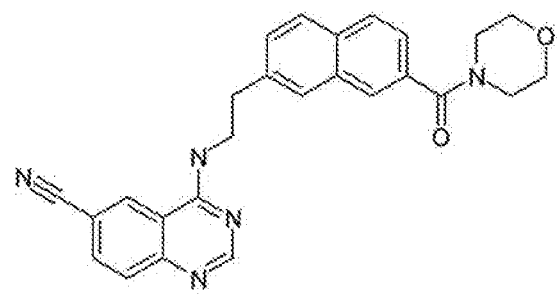
SNX2-1-167
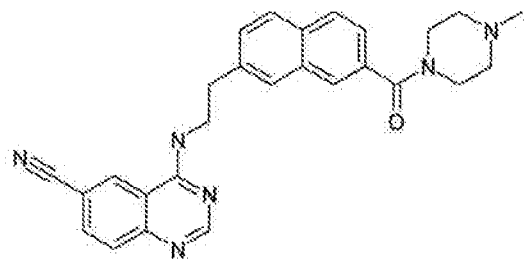
Fig. 1C Figure 5
CDK8
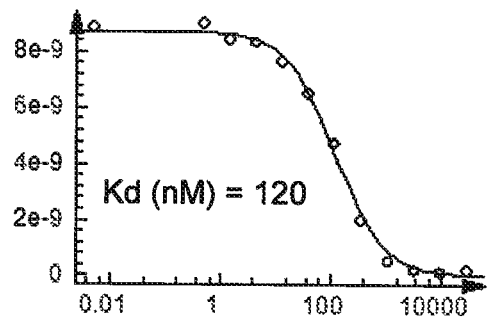 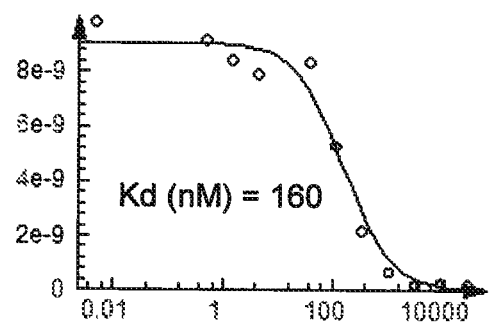
CDK19
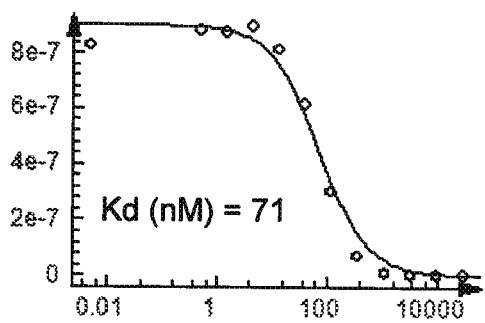 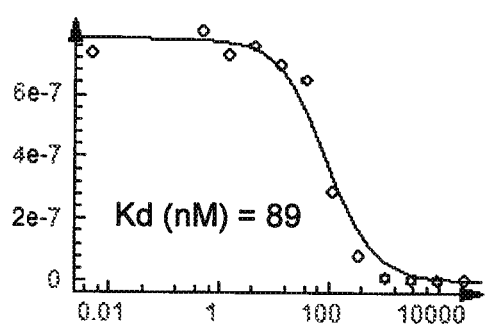
CDK9
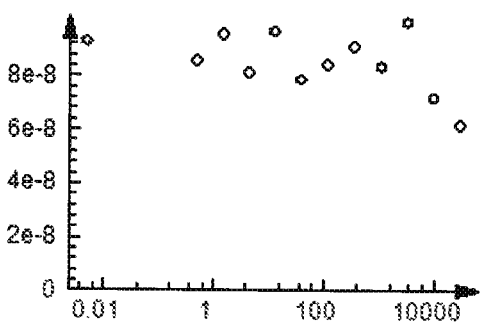 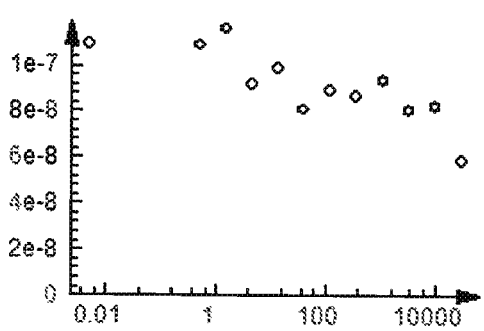

Fig. 9A   Fig. 9B

No invasion                    Invasion

CDK8-CDK19 SELECTIVE INHIBITORS AND THEIR USE IN ANTI-METASTATIC AND CHEMOPREVENTATIVE METHODS FOR CANCER

BACKGROUND OF THE INVENTION

Field of the Invention

The invention relates to the treatment and prevention of cancer.

Summary of the Related Art

CDK8, along with its closely related isoform CDK19, is an oncogenic transcription-regulating kinase (1-3). In contrast to better-known members of the CDK family (such as CDK1, CDK2, and CDK4/6), CDK8 plays no role in cell cycle progression. CDK8 knockout in embryonic stem cells prevents embryonic development (5), due to its essential role in the pluripotent stem cell phenotype (6) but CDK8 depletion does not inhibit the growth of normal cells (5, 7). The role of CDK8 in cancer is due to its unique function as a regulator of several transcriptional programs involved in carcinogenesis (1). CDK8 has been identified as an oncogene in melanoma (8) and colon cancer (7), the CDK8 gene being amplified in ~50% of the latter cancers. Higher expression of CDK8 has been associated with worse prognosis in colon cancer (9). The known cancer-relevant activities of CDK8 include positive regulation of Wnt/β-catenin pathway (7, 11), growth factor-induced transcription (12) and TGFβ signaling (13). CDK8 was also shown to maintain the pluripotent phenotype of embryonic stem cells and has been associated with the cancer stem cell phenotype (6). DNA-damaging chemotherapeutic drugs induce TNFα, an activator of the transcription factor NFκB (14), in endothelial cells and in other cancer-associated stromal elements. Stroma-derived TNFα acts on tumor cells, where it induces NFκB-mediated production of related tumor-promoting cytokines CXCL1 and CXCL2. CXCL1/2 attract myeloid cells to the tumor, by binding to CXCR2 receptor on the myeloid cell surface. Myeloid cells then secrete small calcium-binding proteins S100A8 and A9 that are associated with chronic inflammation and cancer. S100A8/9 act on tumor cells, promoting both their metastasis and survival of chemotherapy (15). PCT/US12/55064 teaches that CDK8/19 inhibitors inhibit induction of transcription factor NFκB, which mediates the production of multiple tumor-supporting proteins and inflammatory cytokines, and that CDK8/19 inhibitors in particular inhibit NFκB-mediated induction of CXCL1 and CXCL2. US Patent Publication 20120071477 teaches that CDK8/19 inhibitors also prevent the induction of paracrine tumor-promoting activities by DNA damage in normal fibroblasts, and inhibit HIV replication and β-catenin signaling.

US patent applications 20040180844 and 20040180848 claim "A method of killing a cancer cell, the method comprising contacting the cancer cell with an inhibitor of a gene selected from the group consisting of CDK8, STK33, PRKCM, PRKACA, ACVR1B, CDK5R1, CDC42BPB, MPP6, and CDC42BPA", on the basis of a finding that transfection with siRNAs targeting CDK8 and certain other genes induces toxicity in a lung carcinoma cell line. However, this observation does not indicate that inhibition of the same genes would not be generally toxic to the organism and does not offer mechanistic rationale for inhibiting CDK8 in cancer treatment.

US Patent Publications 20120071477 discloses selective inhibitors of CDK8 and its isoform, CDK19. There is a need for more soluble and more potent compounds and methods for selectively inhibiting CDK8. There is also a need to better understand the role of CDK8 in cancer to provide additional uses of CDK8 inhibitors.

BRIEF SUMMARY OF THE INVENTION

The invention provides compounds, pharmaceutical formulations and methods for treating degenerative diseases of the central nervous system (including Alzheimer's Disease and other dementias), cancer, viral diseases, atherosclerosis, arthritis and chronic renal disease. In addition, the present inventors have surprisingly discovered that CDK8/19 inhibitors prevent the emergence of cancers (chemoprevention) and prevent cancer recurrence and metastasis by administering these agents after tumor debulking through surgery, chemotherapy or radiation.

The instant invention provides a surprising discovery that treatment of an animal with a CDK8/19 inhibitor prior to injecting tumor cells into the animal reduces the growth rate of tumors that develop subsequently to treatment with the inhibitor. This surprising effect could be due to the inhibition of the expression of those CDK8-regulated genes in normal tissues that support the growth of tumors. The importance of CDK8 expression for the outcome of cancer treatment is further demonstrated in the instant application by the striking associations between high expression of CDK8 and its binding partner, Cyclin C (CCNC) with poor survival in breast cancer patients, and in those ovarian cancer patients whose treatment contained DNA-damaging platinum compounds. These findings indicate that the administration of a small molecule compound that specifically inhibits CDK8/19 should be beneficial for life extension of cancer patients even when such a compound is administered when the bulk of the tumor is not present in the patient, e.g. in the context of chemoprevention or as an adjuvant or anti-recurrence/anti-metastatic therapy following tumor debulking.

These findings further indicate that the measurement of CDK8 expression in cancers provides a diagnostic procedure to identify cancer patients at high risk in general, at risk when treated with DNA-damaging chemotherapeutic, and those patients who are most likely to benefit from treatment with a small molecule compound that specifically inhibits CDK8/19. In some embodiments the cancer patient is breast or ovarian carcinoma patient.

In a first aspect, the invention provides new compounds having enhanced solubility and/or potency for specifically inhibiting Cyclin-Dependent Kinases 8 and 19 (CDK8/CDK19). Initially, the inventors used a high throughput screening system, described in greater detail in application number PCT/US06/01046, to screen over 100,000 drug-like small molecules from commercially available diversified compound collections for the ability to prevent the induction of transcription by a CDK-binding protein p21. Through this screening, the present inventors identified a set of active compounds. (See US Patent Application Publication No. 20080033000.) These included a series of structurally related compounds, which inhibit the induction of transcription by p21, show little or no cytotoxicity in normal cells, and do not interfere with the cell cycle-inhibitory function of CDKIs. The present inventors then discovered a subset of the compounds that selectively inhibit CDK8/CDK19. These were the first such compounds to show such selectivity.

Based upon the above-described results, the present inventors have set out to develop new compounds that retain the benefits of those previously identified compounds while providing even greater solubility and/or potency.

In a second aspect the invention provides methods for inhibiting the production of tumor-promoting secreted factors by fibroblasts, comprising contacting the fibroblast with a small molecule compound that specifically inhibits CDK8/19.

In a third aspect, the compounds and methods according to the invention are useful for treating a CDKI-mediated disease, including but not limited to Alzheimer's disease, atherosclerosis, amyloidosis, arthritis, chronic renal disease, viral diseases and cancer. Thus, the invention provides a method for treating or therapeutically treating a mammal having a CDKI-mediated disease comprising administering to the mammal a therapeutically effective amount of a small molecule compound that specifically inhibits CDK8/19.

In a fourth aspect, the invention provides compounds that inhibit CDK8 to a greater extent than it inhibits certain other CDKs.

In a fifth aspect, the invention provides methods for treating a mammal having a tumor that expresses β-catenin, the method comprising administering to the mammal a novel small molecule compound according to the first aspect of the invention that specifically inhibits CDK8/19.

In a sixth aspect, the invention provides a method for chemoprotecting a patient at risk for developing cancer, comprising administering to the patient a small molecule compound that specifically inhibits CDK8/19.

In a seventh aspect, the invention provides a method for preventing cancer recurrence or metastasis in a cancer patient who has undergone debulking treatment for a tumor, comprising administering to the patient a small molecule compound that specifically inhibits CDK8/19 following debulking. In some embodiments, the patient is an ovarian or breast cancer patient.

In an eighth aspect, the invention provides a method for treating a cancer patient comprising administering to the patient an effective amount of a DNA-damaging agent in combination with a small molecule compound that specifically inhibits CDK8/CDK19. In some embodiments the cancer patient is a breast or ovarian carcinoma patient.

In a ninth aspect, the invention provides a method for improving the efficacy in a patient of adjuvant therapy given in combination with surgery. The method comprises administering a small molecule compound that specifically inhibits CDK8/19 in combination with adjuvant therapy.

In a tenth aspect, the invention provides a method for treating breast cancer in a patient, comprising administering to the patient a small molecule compound that specifically inhibits CDK8/19.

In an eleventh aspect, the invention provides a method for determining whether a cancer patient is suitable to be treated with a DNA-damaging agent, the method comprising determining whether CDK8 is overexpressed in the patient. In some embodiments the cancer patient is an ovarian or breast cancer patient In a twelfth aspect, the invention provides a method for determining the likelihood of recurrence or metastasis of a tumor in a cancer patient, comprising obtaining a sample from the tumor from the patient and determining whether CDK 8 is overexpresssed in the tumor sample. In some embodiments the cancer patient is a breast or ovarian carcinoma patient.

In a thirteenth aspect, the invention provides a method for determining whether of a cancer patient will benefit from adjuvant therapy, comprising determining whether CDK8 is overexpresssed in a tumor sample from the patient.

BRIEF DESCRIPTION OF THE DRAWINGS

FIGS. 1A-1C show the structures of compounds listed in Table 1.

FIG. 5 shows Kd determination for SNX2-1-165 for CDK8, CDK19 and a control CDK (CDK9), each assay carried out in duplicate.

DETAILED DESCRIPTION OF THE PREFERRED EMBODIMENTS

Figure 2:
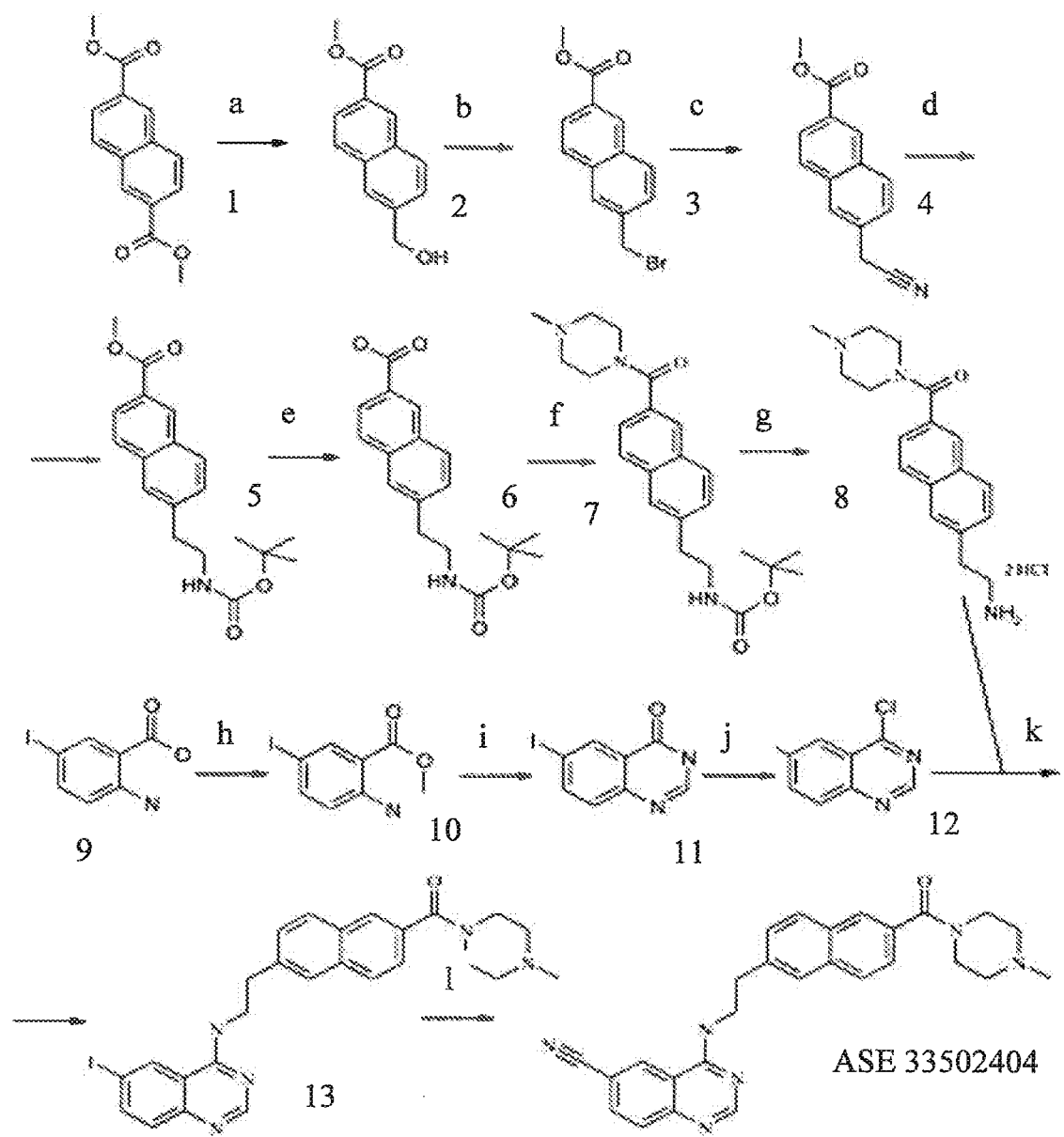
FIG. 2 shows the synthesis scheme for SNX2-1-165.

The invention relates to the inhibition of the Cyclin-Dependent Kinase Inhibitor (CDKI) pathway. More particularly, the invention relates to methods for inhibiting the CDKI pathway for studies of and intervention in senescence-related diseases and cancer.

The invention provides new compounds, pharmaceutical formulations and methods for treating degenerative diseases of the central nervous system, including Alzheimer's Disease and other dementias, as well as cancer, and viral diseases.

The invention provides compounds and methods for inhibiting the CDKI pathway which may have a variety of clinical applications in chemoprevention and therapy of different age-related diseases. The CDKI pathway inhibitors according to the invention show little or no cytotoxicity in normal cells. These molecules do not interfere with the cell cycle-inhibitory function of CDKIs. They also inhibit the secretion of anti-apoptotic factors by CDKI-arrested cells. These compounds selectively inhibit CDK8 and CDK19 with greater solubility and/or potency than previously described.

In various aspects, the invention relates to the treatment of cancer. The present inventors have surprisingly discovered that CDK8/19 inhibitors prevent the emergence of cancers (chemoprevention) and prevent cancer recurrence or metastasis by administering these agents after tumor debulking through surgery, chemotherapy or radiation. The instant invention provides a surprising discovery that treatment of an animal with a CDK8/19 inhibitor prior to injecting tumor cells into the animal reduces the growth rate of tumors that develop subsequently to treatment with the inhibitor. This surprising effect could be due to the inhibition of the expression of those CDK8/19-regulated genes in normal tissues that support the growth of tumors. The instant invention also provides a surprising discovery that treatment of a tumor-bearing animal with a CDK8/19 inhibitor inhibits the invasive growth of the tumor. The importance of CDK8 expression for the outcome of cancer treatment is further demonstrated in the instant application by the striking associations between high expression of CDK8, CDK19 and their binding partner, Cyclin C (CCNC), with the failure of adjuvant therapy to prevent tumor recurrence in breast cancer patients, and in those ovarian cancer patients whose treatment contained DNA-damaging platinum compounds, and with the correlation between high expression of CDK8 and poor relapse-free survival in breast cancer patient regardless of adjuvant therapy. These findings indicate that the administration of CDK8/19 inhibitors should be beneficial for life extension of cancer patients even when such inhibitors are administered when the bulk of the tumor is not present in the patient, e.g. in the context of chemoprevention or as an adjuvant or anti-recurrence/anti-metastatic therapy following tumor debulking.

These findings further indicate that the measurement of CDK8 expression in cancers provide a diagnostic procedure to identify carcinoma patients at high risk in general, at risk when treated with DNA-damaging chemotherapeutic drugs or radiation, and those patients who are most likely to benefit from adjuvant therapy, as well as those patients who are most likely to benefit from treatment that includes CDK8 inhibitors. In some embodiments, the cancer is breast or ovarian cancer. Finally, these findings provide a method for determining the likelihood of recurrence or metastasis of a tumor in a cancer patient, comprising obtaining a sample from the tumor from the patient and determining whether CDK8 is overexpresssed in the tumor sample.

For purposes of the invention, "a small molecule compound that specifically inhibits CDK8/19" is a small molecule compound that inhibits one or more of CDK8 and CDK19 to a greater extent than it inhibits certain other CDKs. In some embodiments, such compounds further inhibit CDK8/19 to a greater extent than CDK9. In preferred embodiments, such greater extent is at least 2-fold more than CDK9. A "small molecule compound" is a molecule having a formula weight of about 800 Daltons or less. Included in compounds that are useful in the invention, except where explicitly stated otherwise, are the compounds described in co-pending US Patent Publication 20120071477 and herein. The terms "SNX-2-165" and "Senexin B" describe the same molecule and are used herein interchangeably. The term "determining whether CDK8 is overexpressed in the sample", and similar terms, means measuring the expression of CDK8 in a tissue (e.g. a tumor sample) or bodily fluid from a patient and comparing it to a standard representing an average level of CDK8 mRNA or protein from normal and/or tumor tissue samples from several other human individuals and/or a non-diseased (e.g. non-cancerous) sample from the patient. "Adjuvant therapy" is radiotherapy and/or systemic therapy (chemotherapy, immunotherapy, biological response modifiers, hormone therapy, and the like, and combinations thereof) given in combination with surgery. (See e.g., as a non-limiting example for breast cancer, emedicine.medscape.com/article/1946040-overview.)

In a first aspect, the invention provides novel small molecule compounds that specifically inhibit CDK8/CDK19, and have improved solubility and/or potency. In some embodiments, the small molecule compound has a structural formula I or II:

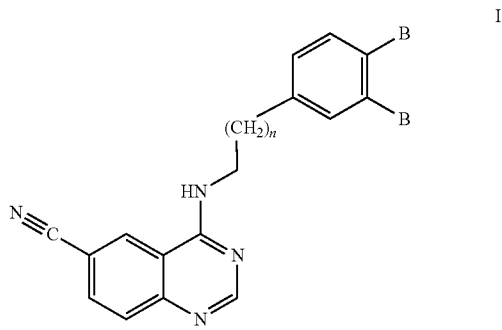

-continued

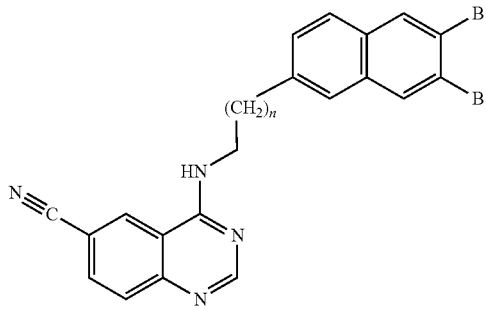

wherein each B is independently hydrogen or

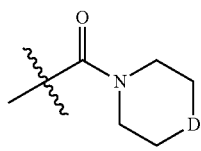

provided that at least one B is hydrogen and not more than one B is hydrogen;
D is selected from —NH, —N-lower alkyl, or O;
and n is 0-2.

In some embodiments, lower alkyl is methyl. In some embodiments, n is 0 or 1. In some embodiments, n is 1.

"Lower alkyl" means an alkyl radical of 1-6 carbon atoms, which may be linear or branched. Some preferred lower alkyl radicals are of 1-3 carbon atoms. In some embodiments, the small molecule compound that specifically inhibits CDK8 and CDK19 is selected from the group consisting of SNX2-1-162, SNX2-1-163, SNX2-1-164, SNX2-1-165, SNX2-1-166 and SNX2-1-167. In some embodiments, the small molecule compound that specifically inhibits CDK8 and CDK19 is SNX2-1-165. In some embodiments, the small molecule compound that specifically inhibits CDK8 and CDK19 is selected from the group of structures shown in FIG. 1.

In a second aspect the invention provides methods for inhibiting the production of tumor-promoting secreted factors by fibroblasts, comprising contacting the fibroblast with a small molecule compound that specifically inhibits CDK8/19.

In certain embodiments, the fibroblast is in a mammal, including a human. It has previously been shown that compounds that specifically inhibit CDK8 inhibit the production of tumor-promoting secreted factors by fibroblasts (See US Patent Publication Number 20120071477).

In a third aspect of the invention, the invention provides a method for treating or therapeutically treating a mammal having a CDKI-mediated disease comprising administering to the mammal an effective or therapeutically effective amount of a small molecule compound that specifically inhibits CDK8/19.

Preferred CDKI-mediated diseases include, without limitation, Alzheimer's disease, other dementias, amyloidosis, atherosclerosis, renal disease, viral diseases, and cancer. In certain embodiments the viral disease is human immunodeficiency virus (HIV) infection. It has previously been shown that compounds that specifically inhibit CDK8 inhibit HIV-1 replication (see United States Patent Publication Number 20120071477). Preferred mammals include a human.

In a fourth aspect, the invention provides small molecule compounds that inhibit CDK8 and CDK19 to a greater extent than they inhibit certain other CDKs. In some embodiments, such compounds further inhibit CDK8 and CDK19 to a greater extent than CDK9. In preferred embodiments, such greater extent is at least 2-fold more than CDK9. Extent of inhibition is measured by the assays taught in the Examples in this specification, including the assay conditions employed by the service providers utilized herein. Results of these assays are commonly expressed herein as percent of control (POC), with the control being no compound being present. Alternatively, the results may be expressed as IC50.

In a fifth aspect, the invention provides methods for treating or therapeutically treating a mammal having a tumor that expresses β-catenin, the method comprising administering to the mammal an effective amount or a therapeutically effective amount of a novel small molecule compound that specifically inhibits CDK8/19. In some embodiments, the novel small molecule compound has a structural formula I or II:

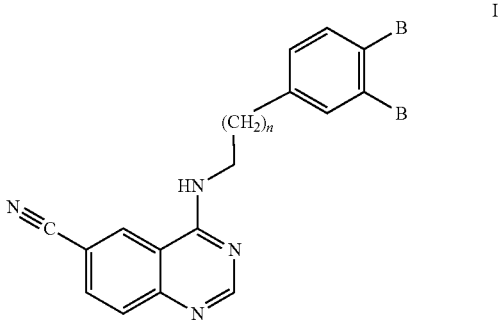

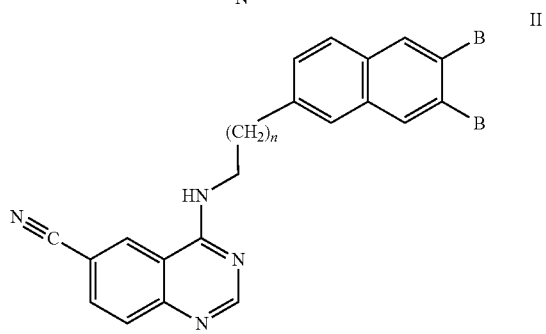

wherein each B is independently hydrogen or

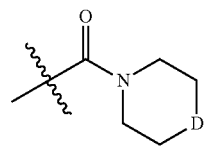

provided that at least one B is hydrogen and not more than one B is hydrogen;
D is selected from —NH, —N-lower alkyl, or O;
and n is 0-2.

In some embodiments, lower alkyl is methyl. In some embodiments, n is 0 or 1. In some embodiments, n is 1.

In some embodiments, the novel small molecule compound is selected from the group consisting of SNX2-1-162, SNX2-1-163, SNX2-1-164, SNX2-1-165, SNX2-1-166 and SNX2-1-167. In some embodiments, the small molecule compound is SNX2-1-165. In some embodiments, the small molecule compound is selected from the group of structures shown in FIG. 1.

It has previously been shown that compounds that specifically inhibit CDK8/19 inhibit the growth of tumor cells that express β-catenin (see United States Patent Publication Number 20120071477). Preferred mammals include a human.

In a sixth aspect, the invention provides a method for chemoprotecting a patient at risk for developing cancer, comprising administering to the patient a small molecule compound that specifically inhibits CDK8/19. A patient at risk for cancer includes individuals who have a familial genetic profile that suggests that cancer is likely to develop. It also includes individuals who have been exposed to carcinogenic agents, such as carcinogenic chemicals or viruses or radiation.

In a seventh aspect, the invention provides a method for preventing cancer metastasis or recurrence in a cancer patient who has undergone debulking treatment for a tumor, comprising administering to the patient a small molecule compound that specifically inhibits CDK8/19 following debulking of the tumor. In some embodiments the cancer patient is breast or ovarian carcinoma patient.

Debulking includes any of the procedures used to treat a primary tumor, such as surgery, chemotherapy and radiation. Despite debulking, there is always a risk of metastasis or incomplete elimination of the primary tumor, resulting in recurrence of the cancer. Administration of a small molecule compound that specifically inhibits CDK8/19 is, therefore, a useful adjuvant therapy to any type of cancer debulking.

In an eighth aspect, the invention provides a method for treating a cancer patient with a DNA damaging agent in combination with a small molecule compound that specifically inhibits CDK8/19. In some embodiments the cancer patient is breast or ovarian carcinoma patient. For purposes of the invention, a DNA damaging agent includes radiation and any chemotherapeutic agent that induces DNA damage, e.g., doxorubicin or platinum based drugs. "In combination with" generally means administering a specific CDK8/19 inhibitor according to the invention and a DNA damaging agent in the course of treating a patient. Such administration may be done in any order, including simultaneous administration, as well as temporally spaced order from a few seconds up to several days apart. Such combination treatment may also include more than a single administration of the compound according to the invention and/or independently the DNA damaging agent. The administration of the compound according to the invention and the other agent may be by the same or different routes.

In a ninth aspect, the invention provides a method for improving the efficacy in a patient of adjuvant therapy given in combination with surgery. The method comprises administering a small molecule compound that specifically inhibits CDK8/19 in combination with adjuvant therapy. "In combination with" generally means administering a specific CDK8/19 inhibitor according to the invention and a DNA damaging agent in the course of treating a patient. Such administration may be done in any order, including simultaneous administration, as well as temporally spaced order from a few seconds up to several days apart. Such combination treatment may also include more than a single administration of the compound according to the invention and/or independently the DNA damaging agent. The administration of the compound according to the invention and the other agent may be by the same or different routes.

In a tenth aspect, the invention provides a method for treating breast cancer in a patient, comprising administering to the patient a specific inhibitor of CDK8/19.

In some embodiments of each of the methods of the second through tenth aspects of the invention, the small molecule compound has a structural formula I or II:

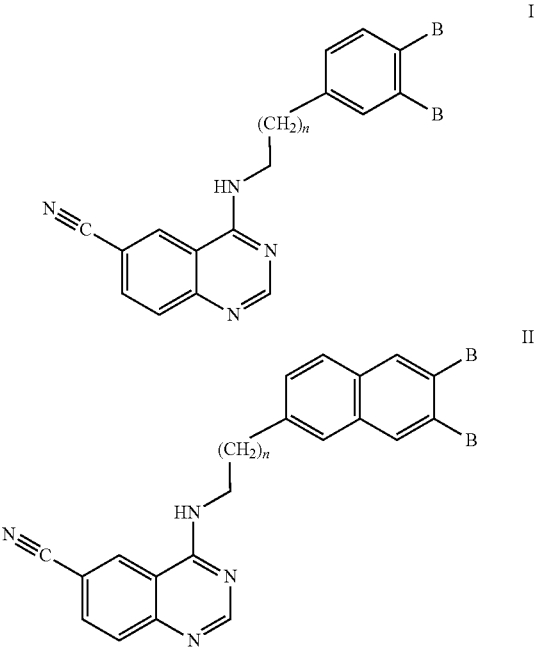

wherein each B is independently hydrogen or

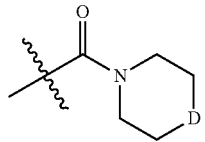

provided that at least one B is hydrogen and not more than one B is hydrogen;
D is selected from —NH, —N-lower alkyl, or O;
and n is 0-2.

In some embodiments, lower alkyl is methyl. In some embodiments, n is 0 or 1. In some embodiments, n is 1.

"Lower alkyl" means an alkyl radical of 1-6 carbon atoms, which may be linear or branched. Some preferred lower alkyl radicals are of 1-3 carbon atoms. In some embodiments, the small molecule compound that specifically inhibits CDK8 and CDK19 is selected from the group consisting of SNX2-1-162, SNX2-1-163, SNX2-1-164, SNX2-1-165, SNX2-1-166 and SNX2-1-167. In some embodiments, the small molecule compound that specifically inhibits CDK8 and CDK19 is SNX2-1-165. In some embodiments, the small molecule compound that specifically inhibits CDK8 and CDK19 is selected from the group of structures shown in FIG. 1.

In some embodiments of each of the methods of treatment or prevention according to the invention, the small molecule compound is administered orally.

In an eleventh aspect, the invention provides a method for determining whether a cancer patient is suitable to be treated with a DNA-damaging agent, the method comprising determining whether CDK8 is overexpressed in a tumor sample from the patient. Determining CDK8 levels prior to treatment should provide valuable information as to whether the use of any of these agents is appropriate, or whether alternative therapeutic approaches should be used. If the patient is determined to not be suitable for treatment with a DNA-damaging agent, the patient may be treated with a DNA-damaging agent incombination with a small molecule compound that specifically inhibits CDK8/19.

In a twelfth aspect the invention provides a method for determining the likelihood of recurrence or metastasis of a tumor in a cancer patient, comprising determining whether CDK8 is overexpresssed in a tumor sample from the patient. In some embodiments the cancer patient is a breast or ovarian carcinoma patient. When it is found that a sample of a tumor that has been surgically removed from a patient has elevated CDK8 expression levels, it may be necessary for the patient to have more frequent follow up testing for recurrence of cancer and/or that the patient requires follow-up treatment according to the seventh aspect of the invention.

In a thirteenth aspect, the invention provides a method for determining the likelihood of whether a cancer patient will benefit from adjuvant therapy, comprising determining whether CDK8 is overexpresssed in a tumor sample from the patient. If the patient is determined to be unlikely to benefit from standard adjuvant therapy, that patient can be treated with adjuvant therapy in combination with a small molecule compound that specifically inhibits CDK8/19.

In alternative embodiments of the foregoing eleventh, twelfth and thirteenth aspects of the invention, instead of, or in addition to determining whether CDK8 is overexpressed in the tumor sample, it is possible to determine whether one or more of CCNC, CDK19, CXCL1 and CXCL2 is overexpressed in the tumor.

Pharmaceutical Formulations and Administration

In the methods according to the invention, the compounds described above may be incorporated into a pharmaceutical formulation. Such formulations comprise the compound, which may be in the form of a free acid, salt or prodrug, in a pharmaceutically acceptable diluent (including, without limitation, water), carrier, or excipient. Such formulations are well known in the art and are described, e.g., in Remington's Pharmaceutical Sciences, 18th Edition, ed. A. Gennaro, Mack Publishing Co., Easton, Pa., 1990. The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. As used herein, the term pharmaceutically acceptable salts refers to salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, poly-glutamic acid, naphthalenesulfonic acid, naphthalenedisulfonic acid, methanesulfonic acid, p-toluenesulfonic acid and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). The active compound is included in the pharmaceutically acceptable carrier or diluent in an amount sufficient to deliver to a patient a therapeutically effective amount without causing serious toxic effects in the patient treated. A "therapeutically effective amount" is an amount sufficient to alleviate or eliminate signs or symptoms of the disease. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art. In certain applications, including without limitation, senile dementias such as Alzheimer's, an effective dose range for a 70 kg patient is from about 50 mg per patient per day up to about 10 grams per patient per day, or the maximum tolerated dose. In certain preferred embodiments the dose range is from about 200 mg per patient per day to about 10 g per patient per day. In certain preferred embodiments the dose range is from about 200 mg per patient per day to about 5 g per patient per day. The dose in each patient may be adjusted depending on the clinical response to the administration of a particular drug. Administration of the pharmaceutical formulations in the methods according to the invention may be by any medically accepted route, including, without limitation, parenteral, oral, sublingual, transdermal, topical, intranasal, intratracheal, or intrarectal. In certain preferred embodiments, compositions of the invention are administered parenterally, e.g., intravenously in a hospital setting. In certain other preferred embodiments, administration may preferably be by the oral route.

The following examples are intended to further illustrate certain preferred embodiments of the invention and are not intended to limit the scope of the invention.

Example 1

Synthesis of CDK8/CDK19 Inhibitors

SNX-2-1-165 was synthesized according to the scheme shown in FIG. 2. All other compounds were synthesized using similar procedures.

Example 2

Testing for CDKI Pathway Inhibition

The compounds described below are shown in Table 1 and the structures of some novel compounds according to the invention are shown in FIG. 1. Compounds SNX2-1-102, SNX2-1-108 and SNX2-1-145 were disclosed in U.S. patent application Ser. No. 12/956,420, and the other compounds were newly synthesized. All the compounds were tested for the ability to inhibit the CDKI pathway in a cellular assay described in our previous patent application PCT/US06/

01046. This assay is based on the induction of green fluorescent protein (GFP) expression from the cytomegalovirus (CMV) promoter in human HT1080 fibrosarcoma cells that express CDKI p21 from an isopropyl-β-thio-galactoside (IPTG)-inducible promoter. The compound activity as a CDKI pathway inhibitor is measured by its ability to prevent the stimulation of the CMV promoter upon the addition of p21-inducing IPTG. CMV promoter activity is measured by the ratio of GFP fluorescence to the relative cell number, as determined by staining cellular DNA with Hoechst 33342. Only compounds showing IC50<10 μM in this assay are included in Table 1 and FIG. 1.

Example 3

Solubility and Activity Testing

The compounds were also tested for solubility in 20% propylene glycol and in water, as follows. Compounds (dry powder) were dissolved in 20% propylene glycol at a concentration of 1 mM at a temperature of 40° C. with occasional vortexing. After 30 min, the solution was centrifuged at 10,000×g for 5 min. Serial dilutions of the cleared supernatant were prepared and used to measure the compound concentrations through OD reading, relative to 1 μM standard solution of the same compound. The results of the measurement were expressed as % solubility of the compound at 1 mM in 20% propylene glycol. To determine water solubility, the compounds (dry powder) were initially dissolved in water at a concentration of 100 mM at a temperature of 40° C. with occasional vortexing. After 30 min, the solution was centrifuged at 10,000×g for 5 min, and the formation of an insoluble pellet was monitored. At subsequent steps, the compound was attempted to be dissolved at lower concentrations, until no pellet was observed after centrifugation, indicating complete solution of the compound. The results of the 20% propylene glycol and water solubility measurements for different compounds are listed in Table 1.

maintaining similar activity, indicating that the side chains of these compounds are likely to make SNX2-class compounds more soluble. At the next stage, we synthesized a set of derivatives of two of the most potent of the earlier compounds, SNX2-1-102 and SNX2-1-108, combining their pharmacophores with side groups of two of the new soluble derivatives, SNX2-1-151 and SNX2-1-153.

After testing these new derivatives, we identified several (SNX2-1-162 through SNX2-1-167) that showed both high activity and solubility (Table 1). The most potent of these compounds, SNX2-1-165 was more active than any of the previously developed SNX2-class compounds.

Example 4

Activity Assay for SNX2-1-165

Figure 3:
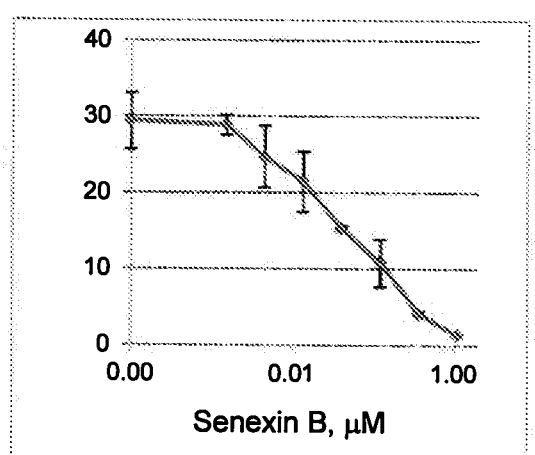
FIG. 3 shows a representative in vitro CDK8 kinase activity inhibition assay for SNX2-1-165 (Senexin B).
Figure 4:
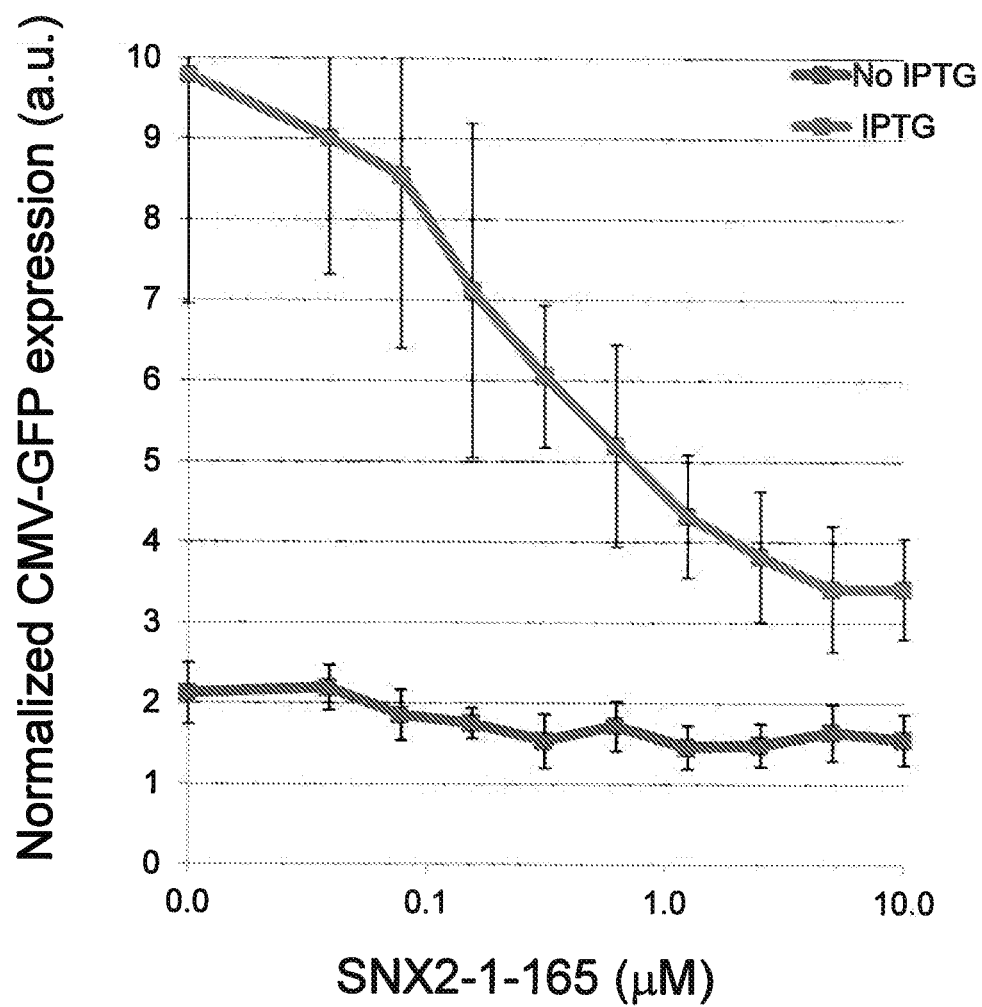
FIG. 4 shows the effect of Senexin B on CDK8 in a cell-based assay for the inhibition of CMV-GFP expression in HT1080 p21-9 cells in the presence of p21-inducing IPTG (upper curve). The lower curve shows the measurements without IPTG addition.

FIG. 3 shows inhibition of CDK8 kinase activity by SNX2-1-165 (Senexin B), as determined using the ProQinase assay kit, providing IC50 values ranging from 24-50 nM in different assays. SNX2-1-165 was fully soluble in 20% propylene glycol at 1 mM, and it was fully soluble in water at 50 mM concentration. Next, the effect of Senexin B on CDK8 was tested in a cell-based assay (inhibition of induction of CMV-GFP expression by IPTG-inducible p21 in HT1080 cells). The results are shown in FIG. 4. Senexin B potently inhibited CDK8 in both assays.

Example 5

Selectivity of SNX2-1-165 for CDK8/CDK19

FIG. 5 shows Kd determination for SNX2-1-165 for CDK8, CDK19 and a control CDK (CDK9), each assay carried out in duplicate. The Kd values were 140 nM for CDK8 and 80 nM for CDK19, whereas CDK9 was not significantly inhibited. The selectivity of SNX2-1-165 for CDK8 and CDK19 was tested using the services of KinomeScan, a division of Ambit Biosciences, San Diego, Calif.,

TABLE 1

Activity and solubility of SNX2-class compounds.

| Compound SNX2-1- | Cell-based Assay EC$_{50}$ (μM) | % solubility at 1 mM in 20% propylene glycol | Water Solubility |
|---|---|---|---|
| Previously reported 102 | 0.66 | 23.1 | Insoluble at 1 mM |
| Previously reported 108 | 1.14 | 38.3 | Insoluble at 1 mM |
| Previously reported 145 | 2.50 | 81 | Insoluble at 1 mM |
| SNX2-1-145 derivative 150 | 2.2 | 100 | Soluble at 10 mM |
| SNX2-1-145 derivative 151 | 3.42 | 100 | Soluble at 10 mM |
| SNX2-1-145 derivative 152 | 3.825 | 100 | Not determined |
| SNX2-1-145 derivative 153 | 5.21 | 100 | Soluble at 10 mM |
| SNX2-1-145 derivative 154 | 9.72 | 100 | Soluble at 10 mM |
| SNX2-1-145 derivative 155 | 4.57 | 100 | Soluble at 10 mM |
| SNX2-1-145 derivative 157 | 2.35 | 100 | Not determined |
| SNX2-1-145 derivative 158 | 2.39 | 100 | Soluble at 10 mM |
| SNX2-1-102 derivative 162 | 0.92 | 100 | Soluble at <50 mM |
| SNX2-1-102 derivative 163 | 1.52 | 100 | Soluble at 50 mM |
| SNX2-1-108 derivative 164 | 0.93 | 100 | Soluble at <50 mM |
| SNX2-1-108 derivative 165 | 0.53 | 100 | Soluble at 50 mM |
| SNX2-1-108 derivative 166 | 1.48 | 100 | Not determined |
| SNX2-1-108 derivative 167 | 1.05 | 100 | Not determined |

Figure 6A:
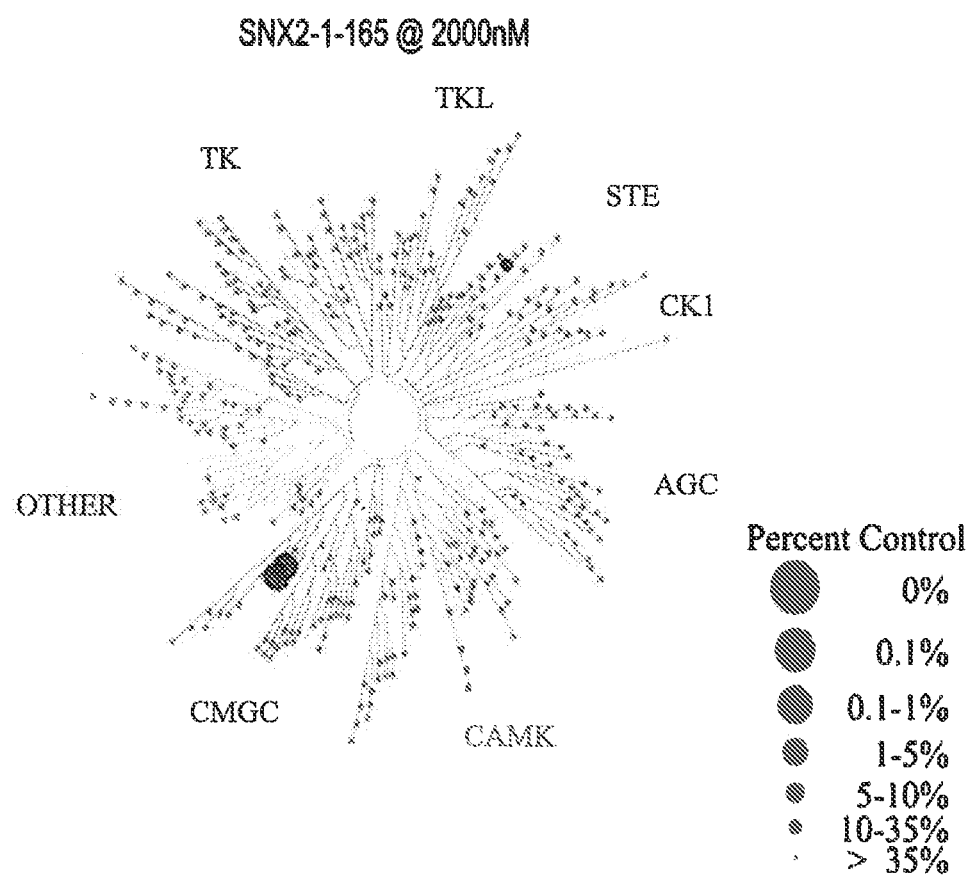
FIG. 6 shows the results of KinomeScan analysis of SNX2-1-165 kinase inhibition selectivity in the form of an evolutionary dendrogram of the kinase family, where kinase inhibition is represented by red circles, the size of which represents the magnitude of the inhibition.
Figure 6B:
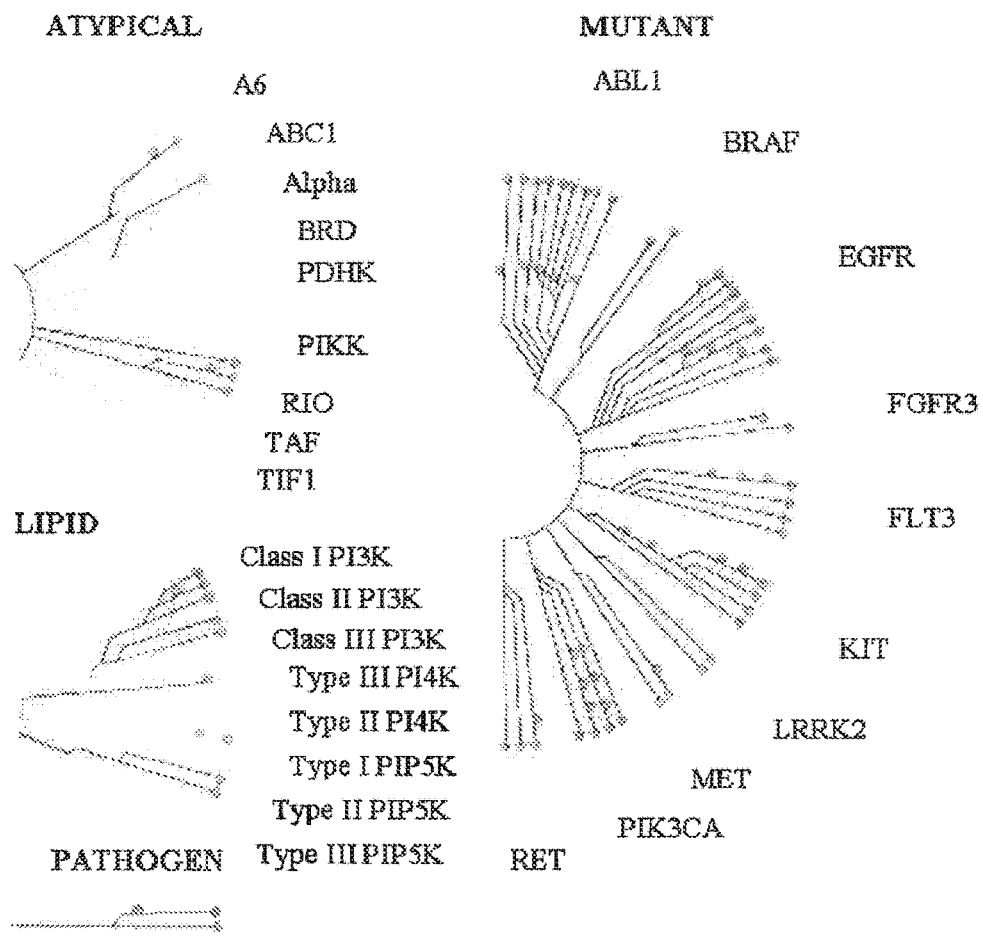

The first set of new compounds was derived from SNX2-1-145. Activity testing showed no major increase in potency relative to SNX2-1-145 for any of these compounds, but solubility testing indicated that several new compounds were much more soluble in water than SNX2-1-145, while which measured the activity of a single concentration of the compound (2,000 nM, an order of magnitude higher than Kd) to inhibit ATP pocket binding of >450 kinases. (16) The results of this analysis are presented in FIG. 6 in the form of an evolutionary dendrogram of the kinase family, where kinase inhibition is represented by red circles, the size of which represents the magnitude of the inhibition. The strongest inhibition was observed for CDK19 (98.6% inhibition) and CDK8 (97.8% inhibition); the only other inhibited kinase shown in FIG. 6 is MAP4K2 (69% inhibition). Aside from YSK4 (59% inhibition), no other kinases in the entire panel were inhibited >50% by 2,000 nM of SNX2-1-165. Hence, SNX2-1-165 is both a highly potent and a highly selective inhibitor of CDK8/19.

Example 6

Senexin B is Nontoxic and Bioavailable in Mice and Rats

Figure 7A:
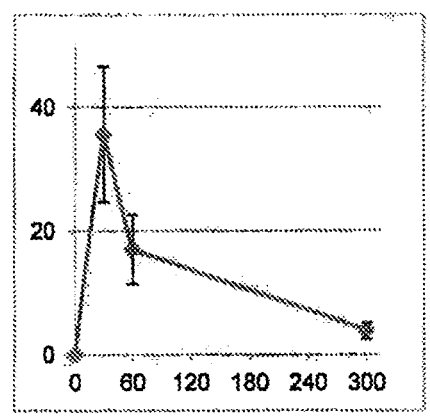
FIG. 7A shows pharmacokinetics (PK) profile of Senexin B in rat plasma after i.p. injection at 40 mg/kg.
Figure 7B:
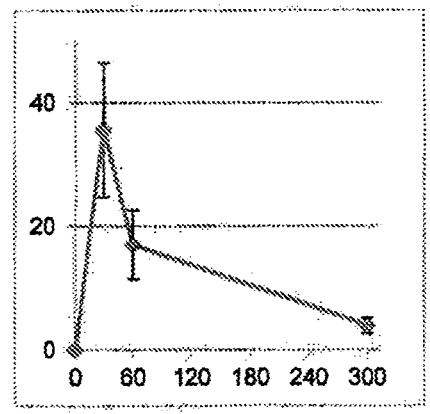
FIG. 7B shows PK profile of Senexin B in mouse plasma, when administered to mice by gavage at 100 mg/kg.

FIG. 7A shows pharmacokinetics (PK) profile of Senexin B in rat plasma after i.p. injection at 40 mg/kg; the area under the curve (AUC) of 14.1 mg*hr/ml was similar to the values for other anticancer drugs, such as recently approved Vemurafenib. When administered to mice by gavage at 100 mg/kg, Senexin B produced peak plasma concentrations of up to ~50 indicating that this compound is orally available (FIG. 7B).

Animal toxicity studies with SNX2-1-165 were conducted as a service by Taconic Farms, Inc. (Hudson, N.Y.). In a 12-day study, two groups of 8 Balb/c mice each received i.p. injections with 5 daily doses of either SNX2-1-165 at 40 mg/kg in an aqueous carrier (10 mM Citric acid, pH 6, 150 mM NaCl) or carrier alone, followed by a 2-day break and another 5 daily doses. Body weight gains of Senexin B-treated mice at the end of the study were indistinguishable from the carrier-treated mice. Among the organs (brain, kidney, thymus, spleen, lung, and liver), only the spleen showed an effect, a weight decrease of ~20%. Blood counts showed only ~25% decrease in lymphocytes and no changes in any other cell types relative to control mice. The tolerability profile of this supra-therapeutic dose suggests that Senexin B has a much wider therapeutic index than typical anti-cancer drugs.

Example 7

SNX2-1-165 Treatment of Animals Inhibits Subsequent Tumor Growth

Figure 8:
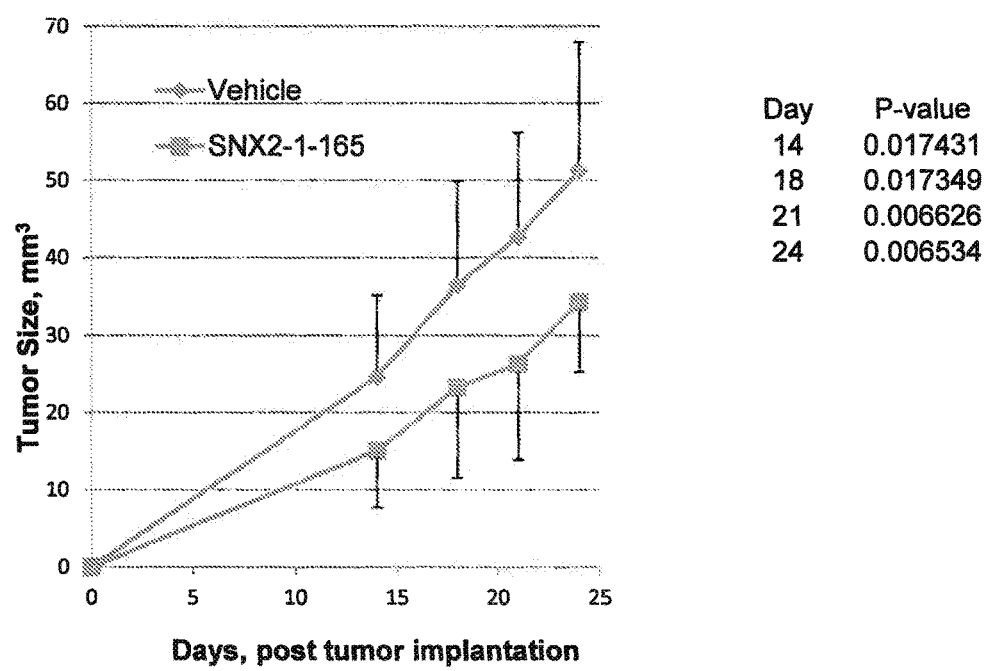
FIG. 8 plots the mean and standard deviation of tumor volumes over time in CB-17 SCID mice treated with 5 daily i.p. injections of SNX2-1-165 (40 mg/kg) or carrier only, then injected s.c. with $1\times10^6$ cells of human A549 lung cancer cell line.

In this study, CB-17 SCID mice (8 weeks old) received 5 daily i.p. injections of SNX2-1-165 (40 mg/kg) or carrier only, 10 mice per group. Mice were then injected s.c. with $1 \times 10^6$ cells of human A549 lung cancer cell line; the tumor cells were injected in the afternoon of the same day when the last dose of treatment was administered in the morning. Starting from day 7 after tumor injection, mice were monitored for tumor formation twice a week, with 3-4 day intervals, until day 24 after tumor injection; tumor volumes were calculated via caliper measurements. By the end of the study, all the mice in both groups developed measurable tumors. FIG. 8 plots the mean and standard deviation of tumor volumes in both groups over time; the table within FIG. 8 shows p-values for the difference in tumor volumes between the two groups (Student t-test). FIG. 8 shows the effect of pretreatment with a CDK8/19 inhibitor SNX2-1-165 on subsequent growth of A549 human lung xenograft tumors in mice. Each point represents mean and standard deviation of tumor volume within a group of 10 mice. Remarkably, mice pretreated with SNX2-1-165 showed significantly slower tumor growth than the control group, reaching p<0.007 on days 21 and 24. Hence, pre-treatment of a tumor-free animal with a CDK8/19 inhibitor inhibits subsequent growth of tumors.

Figure 9:
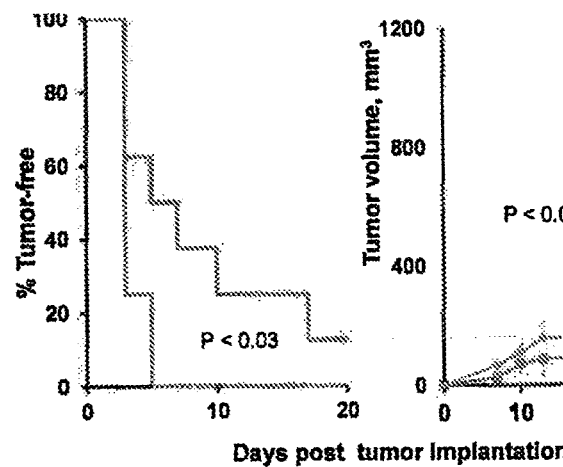
FIG. 9A shows the effect of 5-day pretreatment with 25 mg/kg daily doses of Senexin B (i.p.) on the engraftment of MDA-MB-468 triple-negative breast cancer (TNBC) cells, injected orthotopically in the fat pad of 6-8 week old female nude mice following the last Senexin B treatment.
FIG. 9B shows the results when the mice were treated (daily i.p. injections with 40 mg/kg Senexin B) both before MDA-MB-468 injection (for three days) and after the injection.

Next we tested the effect of 5-day pretreatment with 25 mg/kg daily doses of Senexin B (i.p.) on the engraftment of MDA-MB-468 triple-negative breast cancer (TNBC) cells, injected orthotopically in the fat pad of 6-8 week old female nude mice (4 per group), following the last Senexin B treatment. The appearance of palpable tumors was scored every day. As shown in FIG. 9A, Senexin B-pretreated mice showed significantly slower appearance of palpable tumors at the injection site relative to the control. In the experiment shown in FIG. 9B, mice were treated (daily i.p. injections with 40 mg/kg Senexin B) both before MDA-MB-468 injection (for three days) and after the injection. Caliper measurement of the tumor volumes showed that daily administration of Senexin B produced strong and sustained inhibition of tumor growth (FIG. 9B).

Example 8

Effect of Senexin B on Oncogenic β-Catenin Activity

Figure 10:
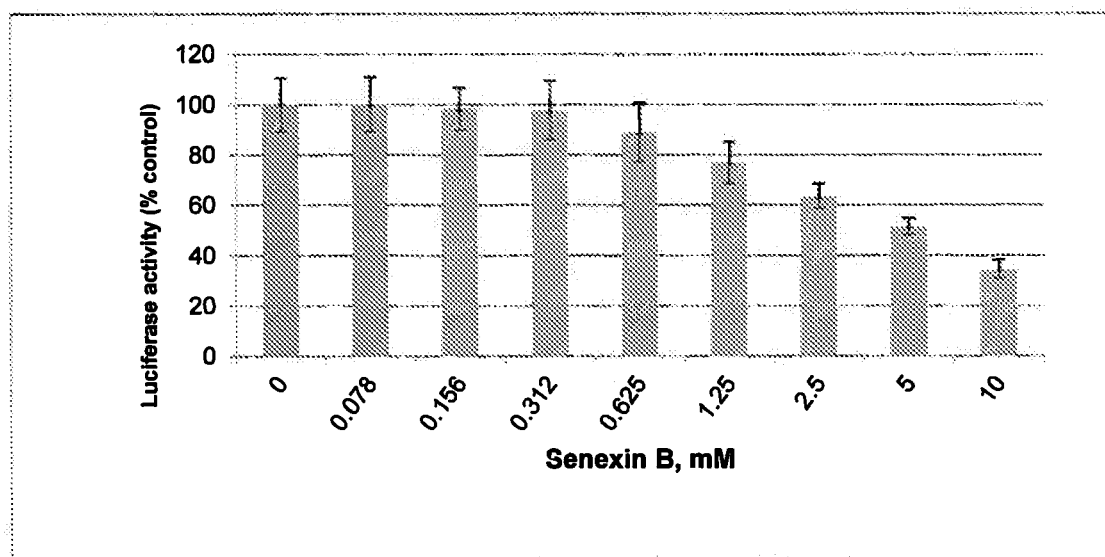
FIG. 10 shows the effect of different concentrations of Senexin B on luciferase expression from the β-catenin-dependent TOPFLASH promoter in HCT116 colon carcinoma cells.
Figure 11A:
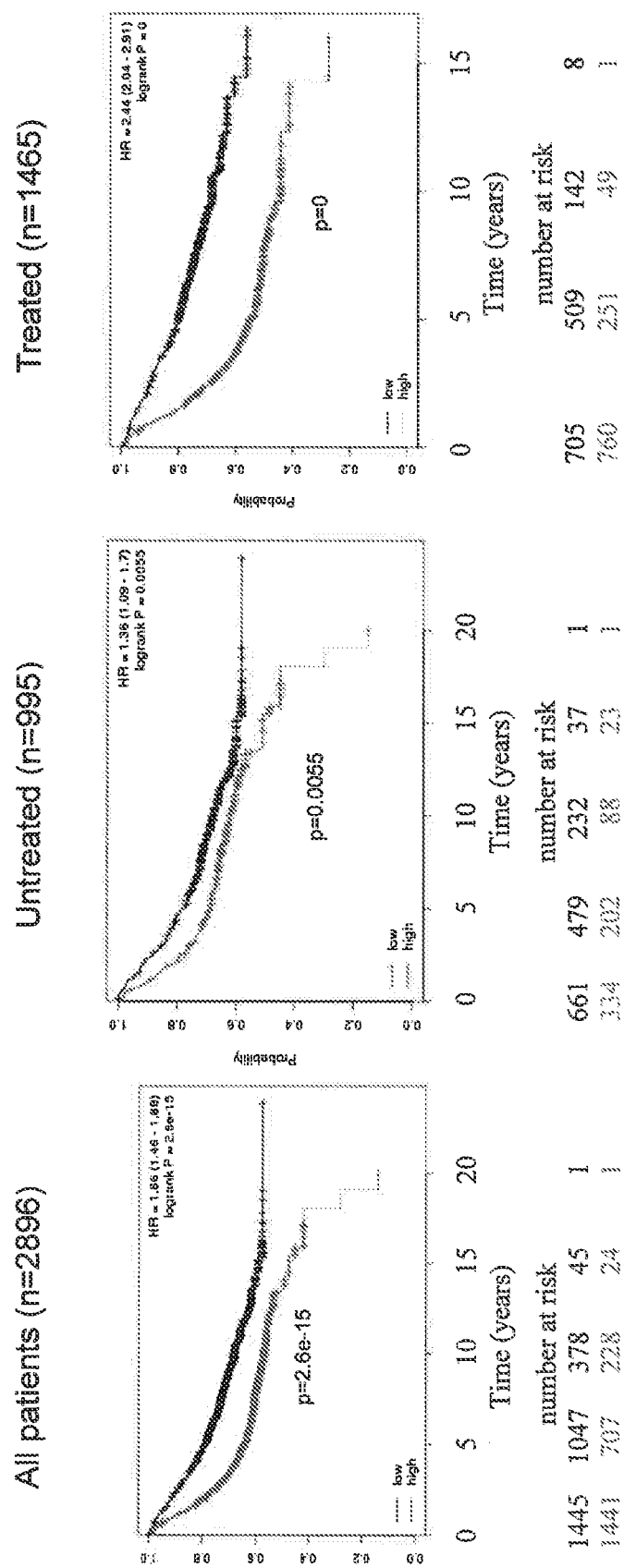
FIG. 11 shows Kaplan-Meier (KM) plots for a correlation between expression of CDK8 and CDK8-associated genes and relapse-free survival (RFS), generated using a web-based program for meta-analysis of gene expression.
Figure 11B:
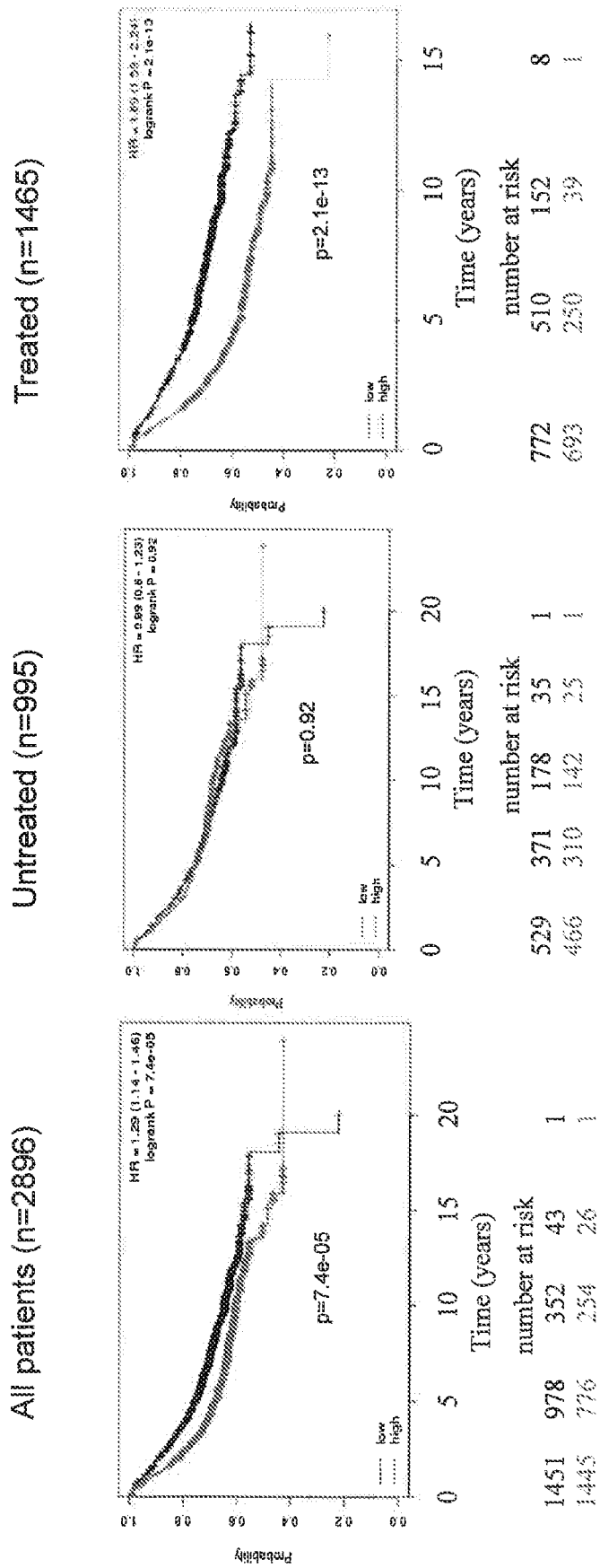
Figure 11C:
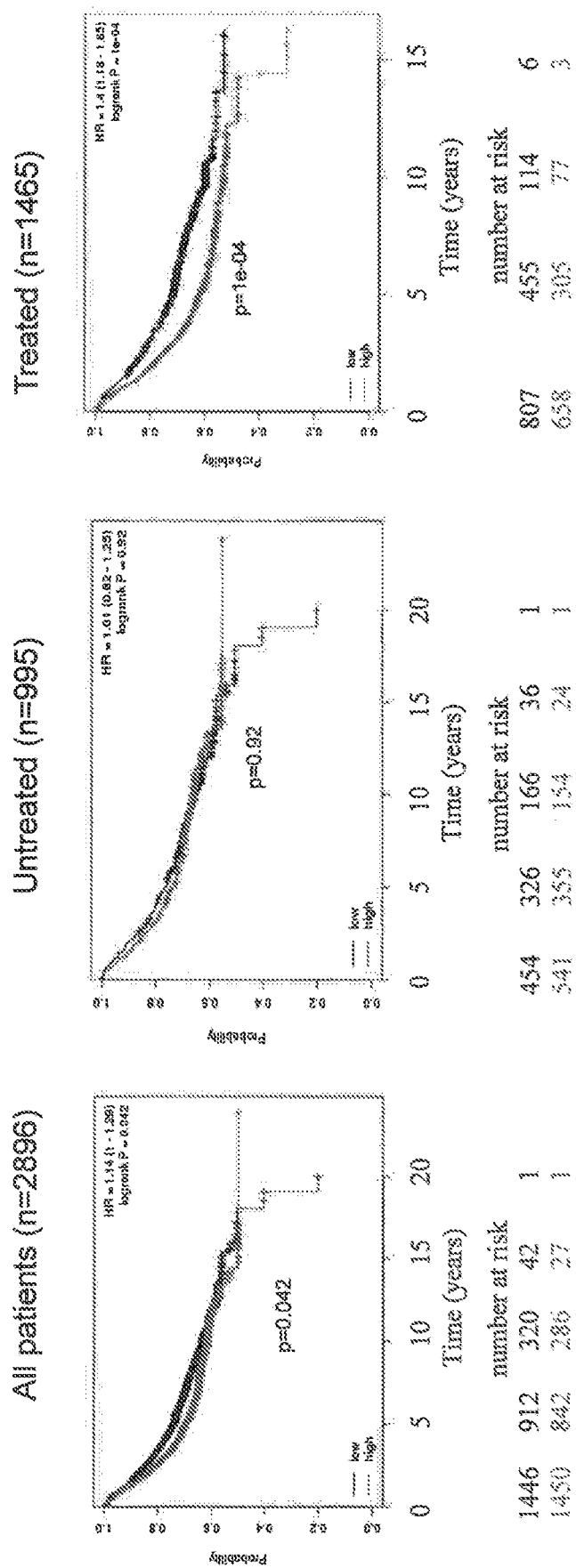
Figure 11D:
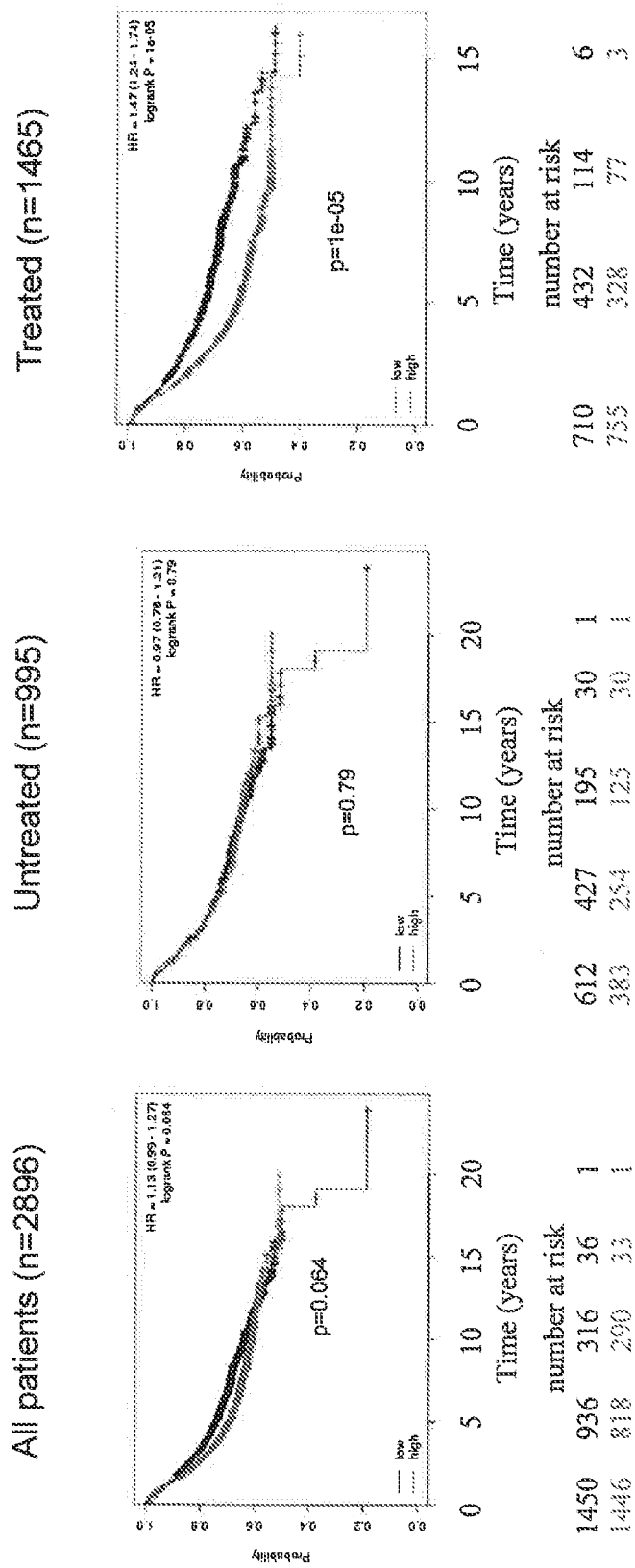
Figure 11E:
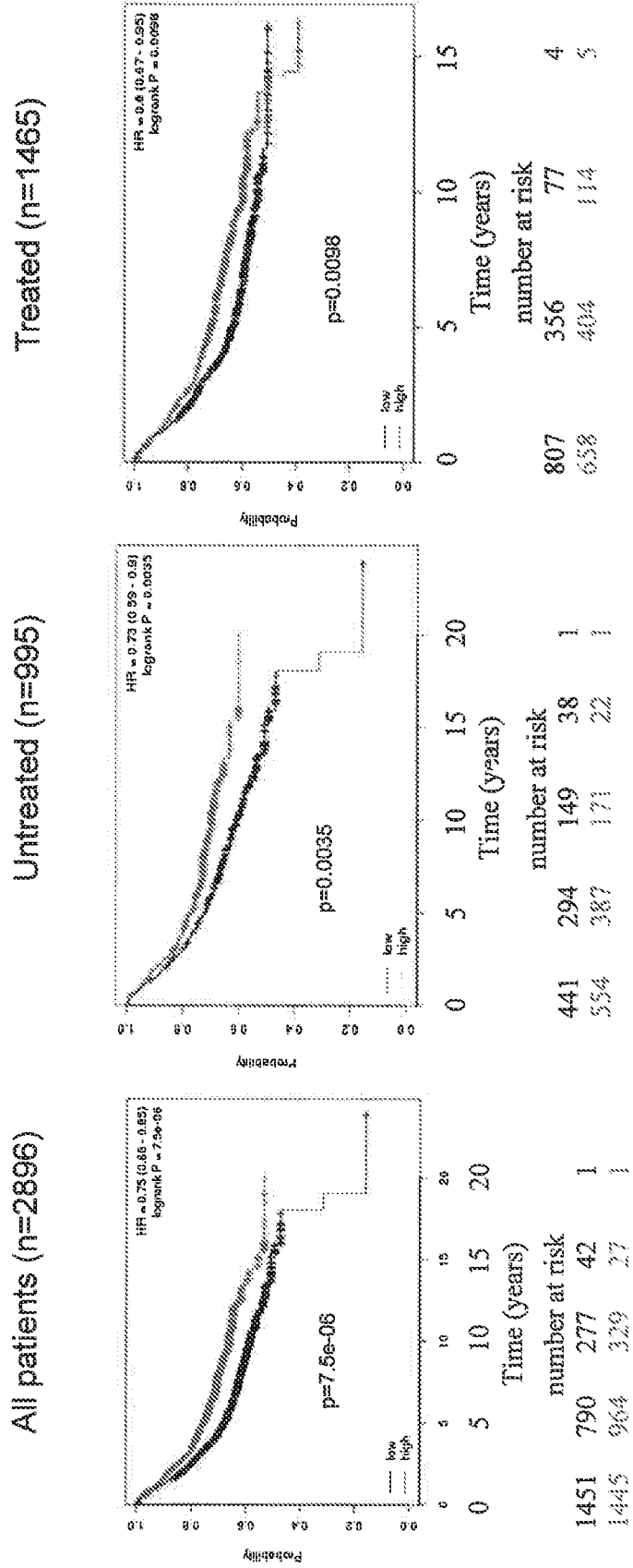

The effect of different concentrations of Senexin B on luciferase expression from β-catenin-dependent TOP-FLASH promoter in HCT116 colon carcinoma cells was measured as described in US Patent Publication 20120071477 for Senexin A (SNX2-1-53). Senexin B shows concentration-dependent inhibition of the oncogenic β-catenin activity (FIG. 10).

Example 9

Effect of CDK8 Expression on Relapse-Free Breast Cancer Survival

To test the impact of CDK8 expression in breast cancer, an online survival analysis tool (http://kmplot.com/analysis/) that evaluates the effect of a gene on prognosis using microarray gene expression data from multiple studies on breast cancer (10) was used. FIG. 11 shows Kaplan-Meier (KM) plots for a correlation between expression of CDK8 and CDK8-associated genes and relapse-free survival (RFS), generated using a web-based program (10) for meta-analysis of gene expression. Affymetrix microarray data from 2,896 breast cancer patients; the JetSet best probeset was chosen for each of the tested genes. Among these patients, 995 were known not to receive adjuvant systemic therapy after sample collection (untreated) and 1,465 received systemic therapy (treated). High expression of CDK8 (as defined by the median value among the 2,896 patients) showed a striking correlation with poor relapse-free survival in all breast cancer patients ($p=2.6 \times 10^{-15}$). This correlation was much weaker among the untreated patients (p=0.0055) but much stronger among the treated patients (p=0), indicating that the negative prognostic impact of CDK8 expression was related to the treatment response to a greater degree than to treatment-independent tumor progression. Similarly, above-median expression of CCNC (Cyclin C, the binding partner of CDK8), CDK19 (a.k.a. CDC2L6, an isoform of CDK8) and MED13 (a protein that interacts with CDK8/CCNC in the CDK module of the Mediator complex (2)) also showed significant correlations among all patients, no correlations among untreated patients and very strong correlations among the treated patients (FIG. 11), indicating that the negative prognostic impact of the expression of these genes was related to the treatment response rather than tumor progression. In contrast, MED12, another subunit of the CDK module of the Mediator showed the opposite correlation, with below-median expression of MED12 strongly associated with shorter RFS. Also in contrast to CDK8 and the other genes in this analysis, MED12 showed similar correlations among the treated and the untreated patients (FIG. 11), indicating that the positive prognostic impact of MED12 expression was related to tumor progression rather than the treatment response. This positive impact of MED12 expression can be explained in light of the recent study (17) that reported that MED12 acts as a negative regulator of TGFβ signaling, an activity independent of its role in the Mediator.

These correlations show that high expression of CDK8, CCNC, CDK18 and MED13 is associated with the failure of adjuvant therapy in breast cancer, and that patients whose tumors show low expression of these genes are especially likely to benefit from adjuvant therapy. In addition, high expression of CDK8 and low expression of MED12 are associated with treatment-independent adverse prognosis in breast cancer. The observed striking clinical correlations for CDK8 expression also suggest that pharmacological inhibition of CDK8 in combination with standard therapy may produce a drastic increase in a patient's disease-free lifespan.

Example 10

Figure 12:
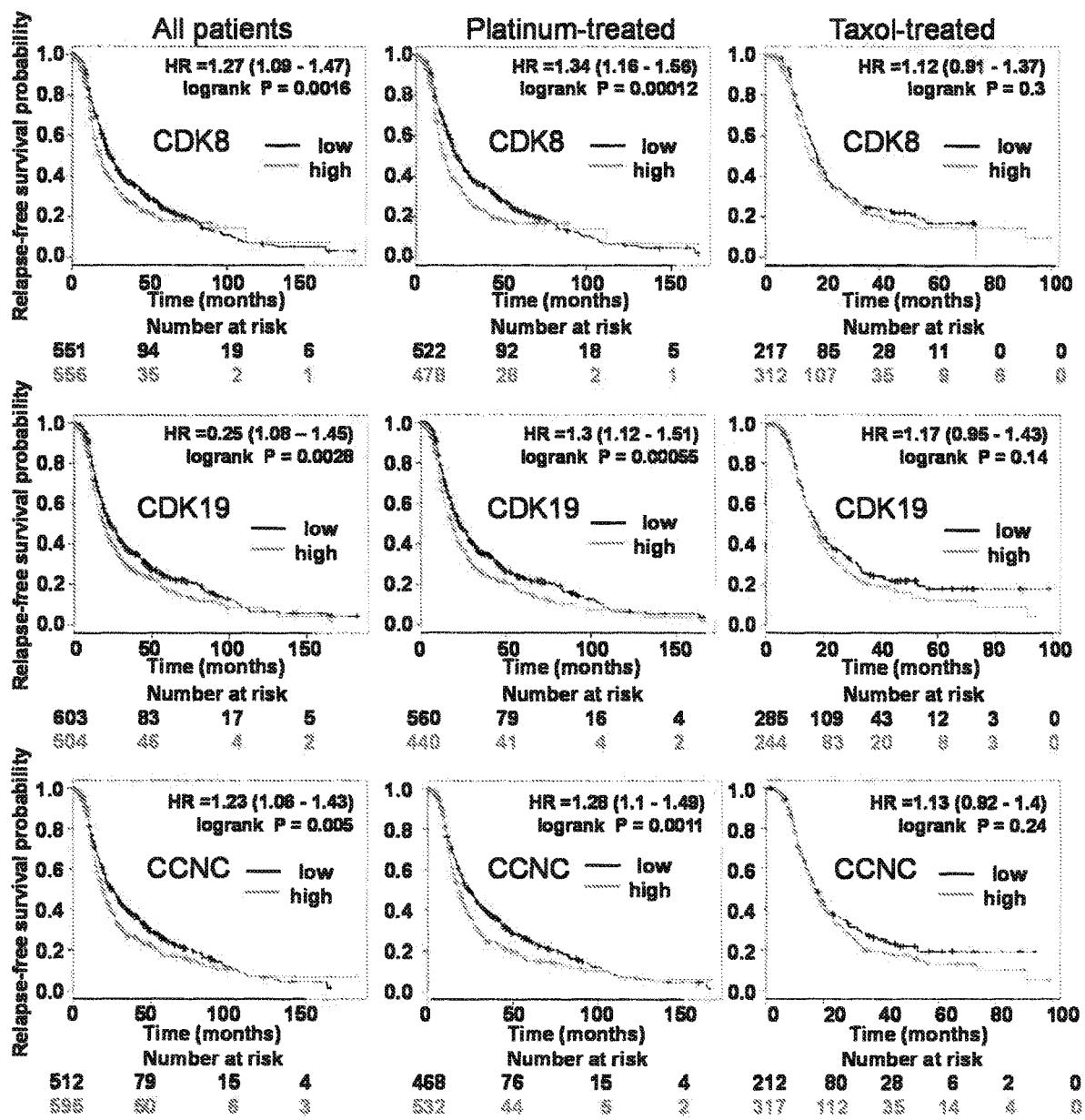
FIG. 12 shows KM plots demonstrating that high expression of CDK8, CDK19 and CCNC significantly correlates with poor survival among ovarian cancer patients, especially those treated with platinum compounds, but not among those treated with taxol.

High CDK8, CDK19 and CCNC Expression is Associated with Tumor Resistance to DNA-Damaging Chemotherapeutic Drugs As described in US Patent Application Publication No. 20080033000, DNA-damaging anticancer agents (such as doxorubicin or ionizing radiation) induce the production of tumor-promoting paracrine activities. This adversarial damage response is inhibited by selective CDK8/19 inhibitors. These findings suggested that tumors expressing high levels of CDK8 may be resistant to DNA-damaging agents due to CDK8-mediated induction of such paracrine activities. The above-mentioned online survival analysis tool (http://kmplot.com/analysis/) contains microarray gene expression data not only from breast cancers but also from 1,107 cases of ovarian cancer, and in the latter case, the tumor samples were stratified by the type of treatment that the patients received (platinum compounds or taxanes). High expression of CDK8, CDK19 and CCNC was significantly correlated with poor survival among ovarian cancer patients, and this correlation became even stronger among 1,000 patients treated with DNA-damaging platinum compounds. Remarkably, the correlation of gene expression with poor survival was lost among 529 patients treated with anti-microtubule drug taxol (FIG. 12). Hence, the expression of CDK8, CDK19, and CCNC is strongly associated with failure of DNA-damaging chemotherapy in clinical cancers. Patients whose tumors express high levels of CDK8, CDK19 or CCNC would be less likely to benefit from treatment with DNA-damaging chemotherapeutic drugs. Low CDK8 expression is associated with about 10 years longer relapse-free survival among all the systemically treated patients. Thus, the role of CDK8 in DNA damage-induced paracrine activities indicates that CDK8 inhibitors can be advantageously combined with DNA-damaging drugs.

Example 11

Immunohistohemical Staining of Breast Cancer Samples

Figure 13A:
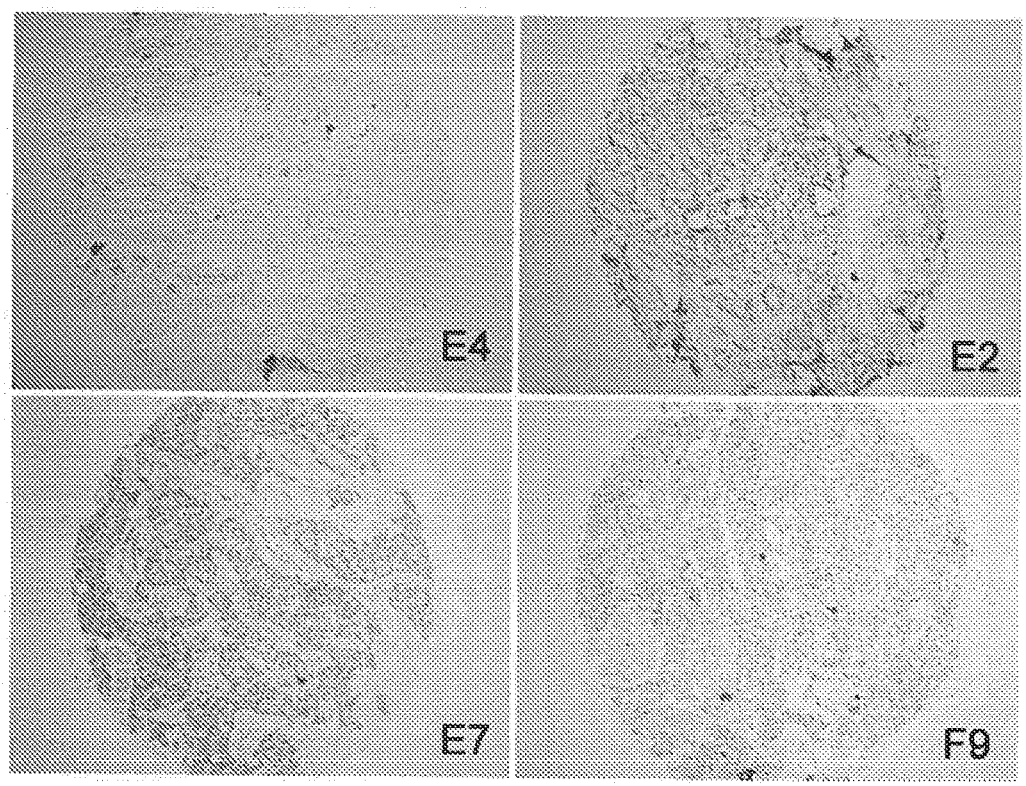
FIG. 13A shows examples of representative staining of invasive intraductal breast cancer sections photographed at 10× objective lens.
Figure 13B:
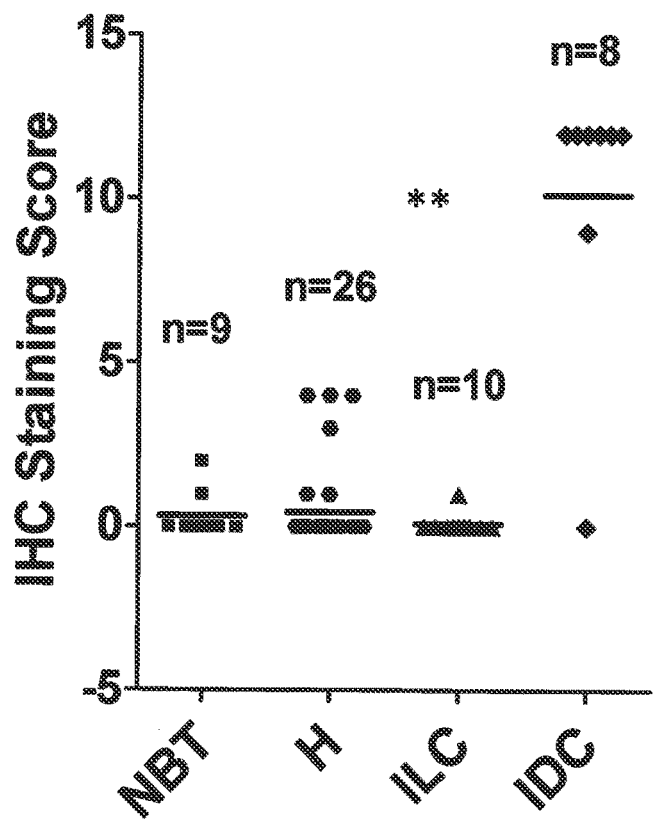
FIG. 13B shows that CDK8 is elevated in invasive ductal carcinomas (IDC) relative to normal (NBT) or hyperplastic (H) breast tissues or intralobular carcinomas (ILC).

CDK8 protein expression was also analyzed in clinical samples of breast cancer, using commercially available breast cancer tissue arrays from US Biomax, comprising formalin-fixed, paraffin-embedded serial sections of breast biopsies on microscopic slides. After washing, epitope unmasking, and peroxidase blocking steps, slides were incubated overnight at 4° C. with antibody against CDK 8 (goat polyclonal, 1:250 dilution; Santa Cruz SC1521), using Antibody Amplifier (ProHisto, LLC). The antibody binding areas were detected by incubation in polymer based secondary donkey anti-goat antibodies (SC-2020, Santa Cruz), 1:2000 diluted, for 1.5 h. Chromogenic detection was accomplished using DAB and counterstaining with methyl green. FIG. 13A shows examples of representative staining of invasive intraductal breast cancer sections (US Biomax BR1003), photographed at 10× objective lens. This analysis indicates that the strongest CDK8 staining is associated with the tumor rather than stromal cells. Immunohistochemical (IHC) analysis of CDK8 protein expression at different stages of breast carcinogenesis shows that CDK8 is elevated in invasive ductal carcinomas relative to normal or hyperplastic breast tissues or intralobular carcinomas (FIG. 13B).

Example 12

Effect of CDK8 Inhibitors Alone on Breast Cancer Cells

Figure 14:
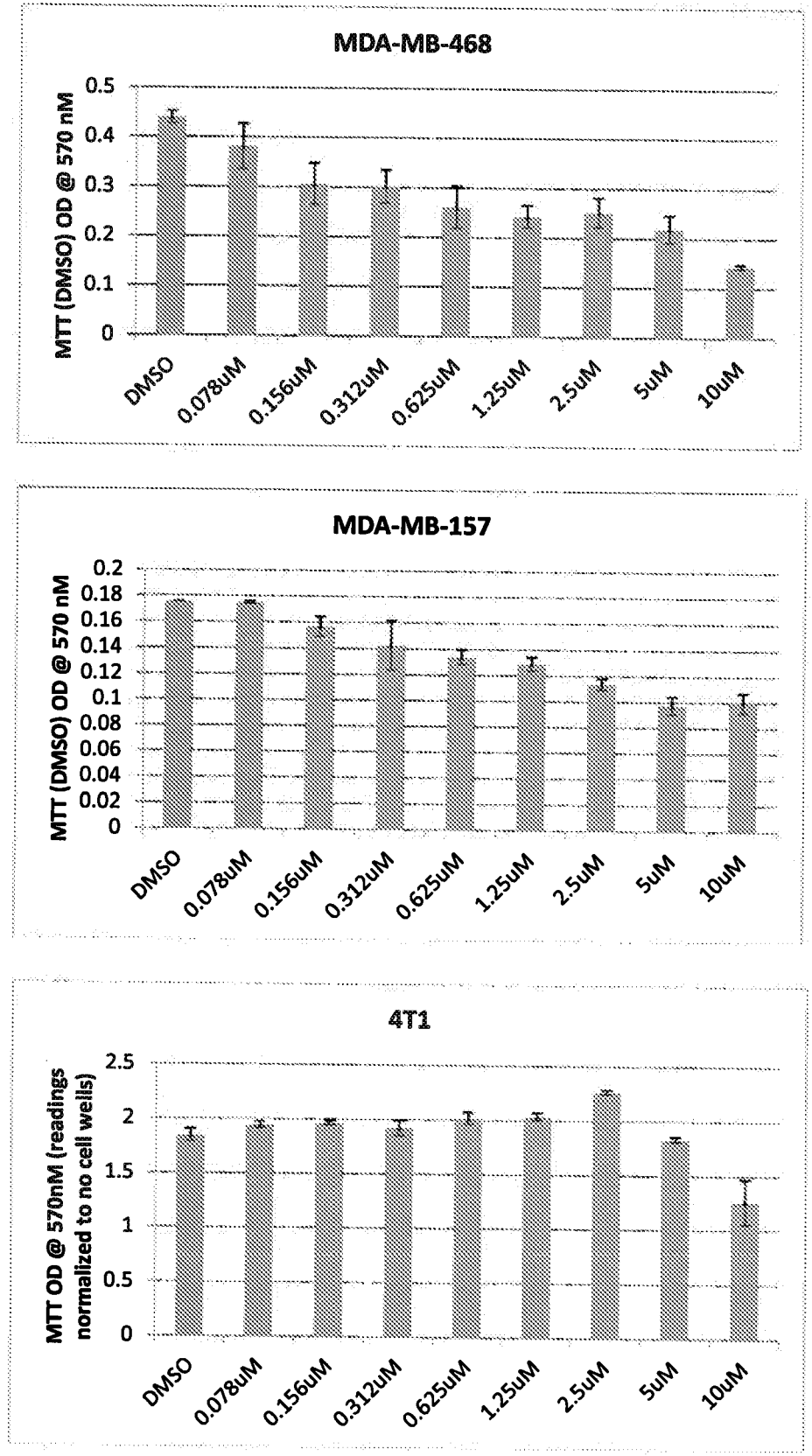
FIG. 14 shows that certain breast cancer cell lines, such as MDA-MB-468 and MDA-MB-157 displayed dose-dependent growth inhibition by SNX2-1-165, while others did not.

With the clinical correlations indicating a critical role for CDK8 in breast cancer, whether the selective CDK8/19 inhibitor SNX2-1-165 would inhibit the growth of different breast carcinoma cell lines in cell culture was tested. Cells were plated in 96-well plates, at 1,500 cells/well, and exposed to carrier or increasing concentrations of SNX2-1-165 (in quadruplicates) for five days; cell survival was measured by the MTT assays. As shown in FIG. 14, certain breast cancer cell lines, such as MDA-MB-468 and MDA-MB-157 displayed dose-dependent growth inhibition by SNX2-1-165, whereas certain others, such as 4T1, were not inhibited except for the highest concentrations of the CDK8/19 inhibitor. These results, together with the correlations of the expression of CDK8, CDK19 and CCNC with poor survival in breast cancer, indicate the utility of CDK8/19 inhibitors for the therapy of breast cancer.

Example 13

Figure 15A:
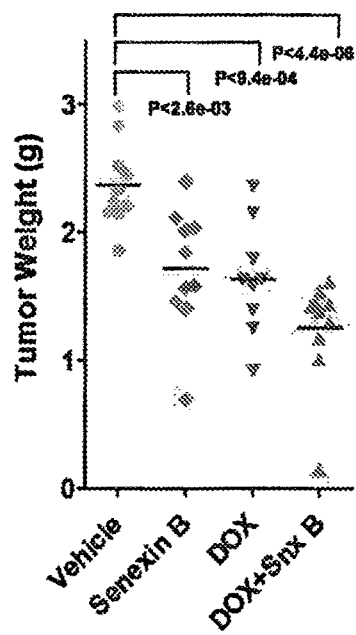
FIG. 15A shows the result of a study with a TNBC line, MDA-MB-231, injected orthotopically into female SCID mice and allowed to form tumors, then treated, at 7-10 day intervals, with three rounds of: vehicle, doxorubicin, Senexin B, or doxorubicin+Senexin.

Senexin B Inhibits Triple-Negative Breast Cancer (TNBC) Xenograft Tumor Growth and Sensitizes TNBC Xenografts to Doxorubicin FIG. 15A shows the result of a study with a TNBC line, MDA-MB-231, injected orthotopically into female SCID mice. Once tumors were formed, mice were randomized into 4 cohorts (n=10) and treated, at 7-10 day intervals, with three rounds of: vehicle (5 daily doses), 1 mg/kg doxorubicin (single dose), 40 mg/kg Senexin B (5 daily doses) or doxorubicin (single dose)+Senexin B (5 daily doses). Although Senexin B was given here only on 15 of 36 days of the treatment period, the group treated with Senexin B alone showed similar reduction in tumor growth as the group treated with doxorubicin alone, as demonstrated by the distribution of tumor weights at the end of the experiment (FIG. 15A). Notably, doxorubicin-treated mice had about 15% lower body weight than the control mice, whereas Senexin B-treated mice showed no significant weight difference from the control, indicating lack of toxicity, despite similar tumor-inhibitory effects of both drugs. Combined treatment with Senexin B and doxorubicin showed an additive effect (FIG. 15A).

Figure 15B:
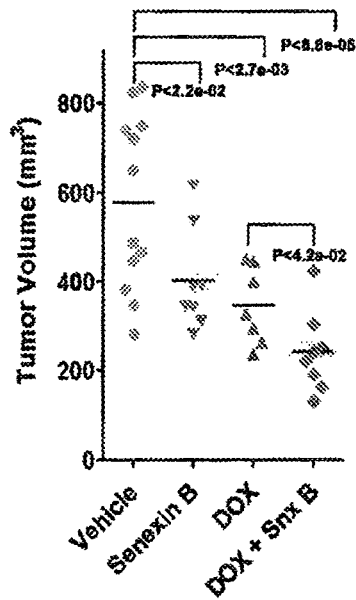
FIG. 15B shows the result of a study using MDA-MB-468 TNBC xenograft model in which female nude mice were inoculated with MDA-MB-468 cells and allowed to form palpable tumors, then treated daily i.p. with vehicle alone, Senexin B, or doxorubicin combined with Senexin B.

FIG. 15B shows the result of a study using MDA-MB-468 TNBC xenograft model. Female nude mice were inoculated with MDA-MB-468 cells, and once palpable tumors were formed, mice were randomized into 4 groups, treated daily i.p. with vehicle alone (n=12), 40 mg/kg Senexin B, two injections with 4 mg/kg doxorubicin two weeks apart, or doxorubicin combined with Senexin B (n=8 in each of the latter groups). FIG. 15B shows the distribution of tumor volumes (caliper measurements) in each group after 30 days of treatment. Both Senexin B and doxorubicin significantly slowed down the tumor growth, and combination of the two treatments produced a significant improvement relative to each individual regimen (FIG. 15B).

Example 14

Senexin B Treatment Inhibits MDA-MB-468 TNBC Tumor Invasion

Figure 16A:
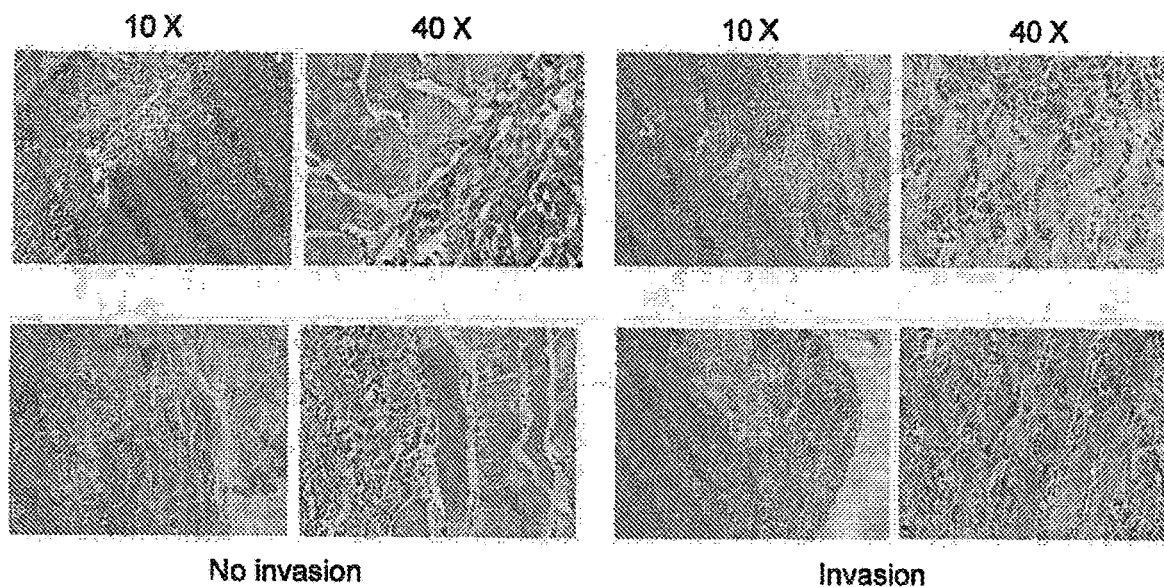
FIG. 16A shows examples of H&E staining of four tumors, photographed with 10× and 40× objectives, and illustrating two cases of non-invasive and two cases of invasive growth.
Figure 16B:
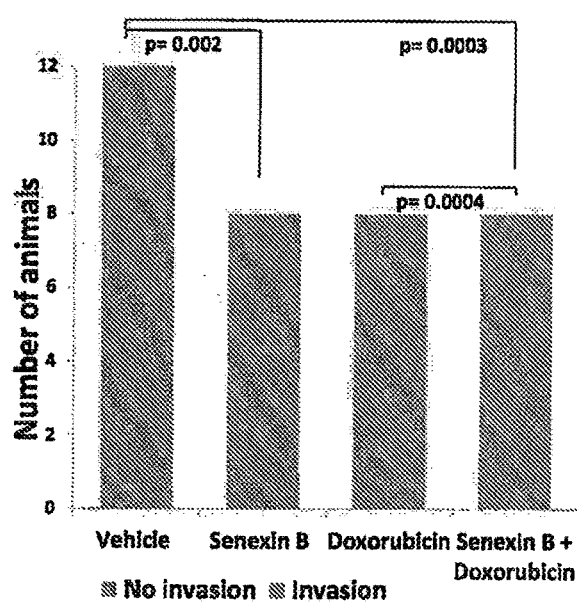
FIG. 16B shows the distribution of invasive and non-invasive growth cases in the groups of mice treated with vehicle alone, Senexin B alone, doxorubicin alone, or doxorubicin and Senexin B, from the experiment in FIG. 15B.

At the end of the experiment shown in FIG. 15B, mice were sacrificed, tumors were removed, formalin fixed, sectioned and processed for histological analysis after H&E staining. This analysis showed that some of the tumors displayed invasive growth into the muscle layer, and others did not invade, leaving clear separation between the tumor and normal tissue areas. FIG. 16A shows examples of H&E staining of four tumors, photographed with 10× and 40× objectives, and illustrating two cases of non-invasive and two cases of invasive growth. FIG. 16B shows the distribution of invasive and non-invasive growth cases in the groups of mice treated with vehicle alone, Senexin B alone, doxorubicin alone, or doxorubicin and Senexin B. The great majority of tumors treated with vehicle alone or doxorubicin alone displayed invasive growth, but almost all the tumors treated with Senexin B, alone or in combination with doxorubicin, were non-invasive. This effect of Senexin B was highly significant, indicating that the CDK8 inhibitor has anti-invasive and therefore anti-metastatic

REFERENCES

1. Xu, W. & Ji, J. Y. (2011) Dysregulation of CDK8 and Cyclin C in tumorigenesis. *J. Genet.* Genomics 38, 439-452.
2. Galbraith, M. D., Donner, A. J., & Espinosa, J. M. (2010) CDK8: a positive regulator of transcription. *Transcription.* 1, 4-12.
3. Firestein, R. & Hahn, W. C. (2009) Revving the Throttle on an oncogene: CDK8 takes the driver seat. *Cancer Res* 69, 7899-7901.
5. Westerling, T., Kuuluvainen, E., & Makela, T. P. (2007) Cdk8 is essential for preimplantation mouse development. *Mol. Cell Biol.* 27, 6177-6182.
6. Adler, A. S., McCleland, M. L., Truong, T., Lau, S., Modrusan, Z., Soukup, T. M., Roose-Girma, M., Blackwood, E. M., & Firestein, R. (2012) CDK8 maintains tumor de-differentiation and embryonic stem cell pluripotency. *Cancer Res.* 72, 2129-2139.
7. Firestein, R., Bass, A. J., Kim, S. Y., Dunn, I. F., Silver, S. J., Guney, I., Freed, E., Ligon, A. H., Vena, N., Ogino, S. et al. (2008) CDK8 is a colorectal cancer oncogene that regulates beta-catenin activity. *Nature* 455, 547-551.
8. Kapoor, A., Goldberg, M. S., Cumberland, L. K., Ratnakumar, K., Segura, M. F., Emanuel, P. O., Menendez, S., Vardabasso, C., Leroy, G., Vidal, C. I. et al. (2010) The histone variant macroH2A suppresses melanoma progression through regulation of CDK8. *Nature* 468, 1105-1109.
9. Firestein, R., Shima, K., Nosho, K., Irahara, N., Baba, Y., Bojarski, E., Giovannucci, E. L., Hahn, W. C., Fuchs, C. S., & Ogino, S. (2010) CDK8 expression in 470 colorectal cancers in relation to beta-catenin activation, other molecular alterations and patient survival. *Int. J. Cancer* 126, 2863-2873.
10. Gyorffy, B., Lanczky, A., Eklund, A. C., Denkert, C., Budczies, J., Li, Q., & Szallasi, Z. (2010) An online survival analysis tool to rapidly assess the effect of 22,277 genes on breast cancer prognosis using microarray data of 1,809 patients. *Breast Cancer Res. Treat.* 123, 725-731.
11. Morris, E. J., Ji, J. Y., Yang, F., Di Stefano, L., Herr, A., Moon, N. S., Kwon, E. J., Haigis, K. M., Naar, A. M., & Dyson, N. J. (2008) E2F1 represses beta-catenin transcription and is antagonized by both pRB and CDK8. *Nature* 455, 552-556.
12. Donner, A. J., Ebmeier, C. C., Taatjes, D. J., & Espinosa, J. M. (2010) CDK8 is a positive regulator of transcriptional elongation within the serum response network. *Nat. Struct. Mol. Biol.* 17, 194-201.
13. Alarcon, C., Zaromytidou, A. I., Xi, Q., Gao, S., Yu, J., Fujisawa, S., Barlas, A., Miller, A. N., Manova-Todorova, K., Macias, M. J. et al. (2009) Nuclear CDKs drive Smad transcriptional activation and turnover in BMP and TGF-beta pathways. *Cell* 139, 757-769.
14. DiDonato, J. A., Mercurio, F., & Karin, M. (2012) NF-kappaB and the link between inflammation and cancer. *Immunol. Rev.* 246, 379-400.
15. Acharyya, S., Oskarsson, T., Vanharanta, S., Malladi, S., Kim, J., Morris, P. G., Manova-Todorova, K., Leversha, M., Hogg, N., Seshan, V. E. et al. (2012) A CXCL1 paracrine network links cancer chemoresistance and metastasis. *Cell* 150, 165-178.
16. Fabian et al., *Nat. Biotechnol.* 23, 329-336, 2005.
17. Huang et al. (*Cell* 151, 937-950, 2012)

What is claimed is:

1. A method for preventing breast cancer recurrence or metastasis in a breast cancer patient who has undergone debulking treatment for a tumor, comprising administering to the patient a small molecule compound that specifically inhibits CDK8/19 following debulking.

2. A method for preventing tumor invasion in a breast cancer patient, comprising administering to the patient a small molecule compound that specifically inhibits CDK8/19.

3. A method for treating a breast cancer patient comprising administering to the patient a small molecule compound that specifically inhibits CDK8/19 in combination with a DNA damaging agent.

4. A method for treating breast cancer in a patient, comprising administering to the patient a small molecule compound that specifically inhibits CDK8/19.

* * * * *